(12) United States Patent
Majima et al.

(10) Patent No.: US 10,564,164 B2
(45) Date of Patent: Feb. 18, 2020

(54) FLUORESCENT PROBE, SINGLET OXYGEN DETECTION AGENT, AND SINGLET OXYGEN DETECTION METHOD

(71) Applicant: Osaka University, Suita-shi, Osaka (JP)

(72) Inventors: Tetsuro Majima, Suita (JP); Sooyeon Kim, Suita (JP); Takashi Tachikawa, Kobe (JP); Mamoru Fujitsuka, Suita (JP)

(73) Assignee: Osaka University, Osaka (JP)

( * ) Notice: Subject to any disclaimer, the term of this patent is extended or adjusted under 35 U.S.C. 154(b) by 640 days.

(21) Appl. No.: 15/320,162

(22) PCT Filed: Jun. 17, 2015

(86) PCT No.: PCT/JP2015/067522
§ 371 (c)(1),
(2) Date: Aug. 22, 2017

(87) PCT Pub. No.: WO2015/194606
PCT Pub. Date: Dec. 23, 2015

(65) Prior Publication Data
US 2017/0363636 A1  Dec. 21, 2017

(30) Foreign Application Priority Data
Jun. 17, 2014  (JP) ................... 2014-124543

(51) Int. Cl.
*C07F 7/10* (2006.01)
*G01N 33/58* (2006.01)

(52) U.S. Cl.
CPC .......... *G01N 33/582* (2013.01); *C07F 7/10* (2013.01)

(58) Field of Classification Search
None
See application file for complete search history.

(56) References Cited

U.S. PATENT DOCUMENTS

| | | |
|---|---|---|
| 6,525,088 B1 | 2/2003 | Nagano et al. |
| 7,524,974 B2 | 4/2009 | Nagano et al. |
| 2004/0043498 A1 | 3/2004 | Nagano et al. |
| 2005/0123478 A1 | 6/2005 | Nagano et al. |
| 2006/0030054 A1 | 2/2006 | Nagano et al. |
| 2014/0342384 A1 | 11/2014 | Nagano et al. |
| 2015/0238085 A1 | 8/2015 | Inoue et al. |
| 2015/0353585 A1 | 12/2015 | Nagano et al. |

FOREIGN PATENT DOCUMENTS

| | | |
|---|---|---|
| JP | 4373608 B | 11/2009 |
| WO | WO 2002/018362 A1 | 7/2002 |
| WO | WO 2004/005917 A1 | 1/2004 |
| WO | WO 2010/126077 A1 | 11/2010 |
| WO | WO 2012/029609 A1 | 3/2012 |
| WO | WO 2012/111818 A1 | 8/2012 |
| WO | WO 2014/030344 A1 | 2/2014 |
| WO | WO 2014/106957 A1 | 7/2014 |

OTHER PUBLICATIONS

S. Kim, et al., "Far-Red Fluorescense Probe for Monitoring Singlet Oxygen during Photodynamic Therapy," Journal of the American Chemical Society, vol. 136, No. 3, pp. 11707-11715 (2014).
A. Castano, et al, "Photodynamic therapy and anti-tumour immunity," Nature Reviews Cancer, vol. 6, No. 7, pp. 535-545 (2006).
J. Snyder, et al, "Optical detection of singlet oxygen from single cells," Physical Chemistry Chemical Physics, vol. 8, pp. 4280-4293 (2006).
X. Li, et al, "Design Strategies for Water-Soluble Small Molecular Chromogenic and Fluorogenic Probes," Chemical Reviews, vol. 114, No. 1, pp. 590-659 (2014).
S. Kim, et al, "Photochemistry of Singlet Oxygen Sensor Green," The Journal of Physical Chemistry B, vol. 117, No. 45, pp. 13985-13992 (2013).
Molecular Probes®, "Product Information: Singlet Oxygen Sensor Green Reagent", Revised: Jan. 30, 2004 (2 pages).

*Primary Examiner* — Heidi Reese
(74) *Attorney, Agent, or Firm* — Lynda L. Calderone; Calderone Bullock, LLC

(57) ABSTRACT

An object of the present invention is to provide a fluorescent probe that easily penetrates a cell and is capable of selectively and efficiently detecting singlet oxygen generated in the cell, a singlet oxygen detection agent containing the fluorescent probe, and a singlet oxygen detection method using the fluorescent probe. The fluorescent probe for detecting singlet oxygen comprises a compound having a silicon-rhodamine skeleton and a skeleton that increases the fluorescence of the fluorescent probe after trapping singlet oxygen to be greater than the fluorescence before trapping singlet oxygen, or a salt, hydrate, or solvate thereof.

18 Claims, 8 Drawing Sheets

FLUORESCENT PROBE, SINGLET OXYGEN DETECTION AGENT, AND SINGLET OXYGEN DETECTION METHOD

BACKGROUND OF THE INVENTION

Field of the Invention

The present invention relates to a fluorescent probe, a singlet oxygen detection agent, or a singlet oxygen detection method.

Description of Related Art

Singlet oxygen ($^1O_2$) is an active species that attacks various molecules having unsaturated bonds or electron-rich molecules, and is used in various applied technologies, such as precise chemical synthesis, polymer science, photodynamic therapy (which hereinafter may also be referred to as "PDT"), wastewater or sludge treatments, and the like. Therefore, singlet oxygen is attracting attention.

PDT, as one of these technologies, is a method for treating diseased tissues of humans or other animals. The method is used to treat cancers and other diseases, and is performed by administrating a photodynamic therapeutic agent containing a photosensitizing substance, which generates reactive oxygen species, such as singlet oxygen, in response to light irradiation, to a patient through, for example, intravenous injection, and then locally irradiating the diseased tissue with light, thereby destroying only the diseased tissue by the generated reactive oxygen species.

The events that first occur after light irradiation during PDT are the generation and diffusion of singlet oxygen, as well as its reaction with peripheral molecules; these processes are considered to be closely related to the cytotoxicity of PDT (for example, see Non-patent Document 1, etc.). In actual medical practice, real-time observation of the generation and changes of singlet oxygen is very important to accomplish the fusion of diagnostic imaging and treatment (theragnostics), because the total amount of singlet oxygen generated by PDT directly influences the treatment progress, treatment efficiency, or the like.

Therefore, several singlet oxygen detection methods, typically a method for measuring the phosphorescence of singlet oxygen itself or a method using a fluorescent probe that produces luminescence by reacting with singlet oxygen, have been performed (for example, see Non-patent Documents 2, 3, etc.).

However, the method for measuring the phosphorescence of singlet oxygen itself requires the detection of low-energy phosphorescence, and therefore requires a special detector. This makes the method unrealistic; further, the spatial resolution is merely a single cell level (for example, see Non-patent Document 2, etc.).

In contrast, fluorescent probes for singlet oxygen detection enable the detection more easily than that in the measurement of phosphorescence of singlet oxygen itself, and therefore have been widely used.

CITATION LIST

Non-Patent Documents

Non-patent Document 1: A. P. Castano et al., Nat. Rev. Cancer 6, 535-545 (2006)

Non-patent Document 2: J. W. Snyder et al., Phys. Chem. Chem. Phys. 8, 4280-4293 (2006)

Non-patent Document 3: X. Li et al., Chem. Rev. 114, 590-659 (2014)

Non-patent Document 4: T. Majima et al., J. Phys. Chem. B 117, 13985-13992 (2013)

BRIEF SUMMARY OF THE INVENTION

Technical Problem

However, Singlet Oxygen Sensor Green (Molecular Probes®; which hereinafter may also be referred to as "SOSG"), which is commercially available and most commonly used as a fluorescent probe for singlet oxygen detection, has inadequate cell permeability; it also inactivated by self-oxidation. Therefore, the probe is incapable of site-selective detection of singlet oxygen generated in a cell, and thus is problematic in the use as a fluorescent probe (for example, see Non-patent Document 4, etc.). Further, this previously known SOSG also has a problem of defective detection of singlet oxygen because it produces luminescence by blue light irradiation (i.e., it requires the emission of high-energy light), thereby inevitably causing luminescence of the cell itself. Therefore, the number of reports regarding fluorescent probes capable of intracellular singlet oxygen detection is significantly fewer than that of fluorescent probes for detecting other reactive oxygen species; further, the most commonly used commercially-available probe also has drawbacks. Thus, currently, there are no fluorescent probes for singlet oxygen detection that can ensure high intracellular site-selectivity with respect to a photosensitizer.

Accordingly, an object of the present invention is to provide a fluorescent probe that easily penetrates cells and is capable of selectively and efficiently detecting singlet oxygen generated in the cell, a singlet oxygen detection agent containing the fluorescent probe, and a singlet oxygen detection method using the fluorescent probe.

Solution to Problem

The inventors of the present invention conducted extensive research to achieve the above object, and found that a compound group, which has a silicon-rhodamine skeleton and a skeleton that increases the fluorescence of a fluorescent probe after trapping singlet oxygen to be greater than that before the trapping of singlet oxygen, can penetrate mitochondria, which is the main target organelle in PDT, and therefore can serve as a red fluorescent probe capable of site-selectively detecting singlet oxygen generated from a photosensitizer coexisting in the mitochondrial inner membrane. The present invention was completed by further research based on this finding. Specifically, the present invention encompasses the following structures.

Item 1. A fluorescent probe for detecting singlet oxygen, comprising a compound having a silicon-rhodamine skeleton and a skeleton that increases the fluorescence of the fluorescent probe after trapping singlet oxygen to be greater than the fluorescence before trapping singlet oxygen, or a salt, hydrate, or solvate thereof.

Item 2. The fluorescent probe according to Item 1, wherein the compound is represented by Formula (1):

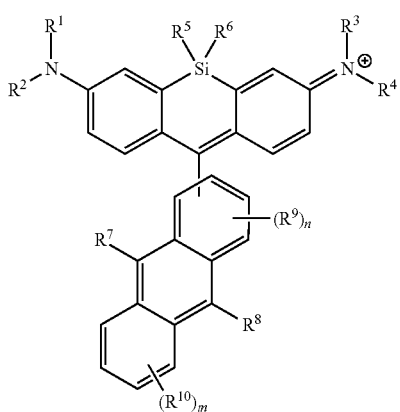

wherein $R^1$ to $R^4$ are the same or different, and each represents hydrogen, substituted or unsubstituted alkyl, substituted or unsubstituted alkenyl, substituted or unsubstituted alkynyl, or substituted or unsubstituted aryl; $R^5$ and $R^6$ are the same or different, and each represents hydrogen, hydroxy, halogen, substituted or unsubstituted alkyl, substituted or unsubstituted alkenyl, substituted or unsubstituted alkynyl, or substituted or unsubstituted aryl; $R^7$ and $R^8$ are the same or different, and each represents hydrogen, halogen, substituted or unsubstituted alkyl, substituted or unsubstituted alkenyl, substituted or unsubstituted alkynyl, substituted or unsubstituted aryl, substituted or unsubstituted alkoxy, or acid addition salt; $R^9$ and $R^{10}$ are the same or different, and each represents hydrogen, hydroxy, halogen, substituted or unsubstituted alkyl, substituted or unsubstituted alkenyl, substituted or unsubstituted alkynyl, substituted or unsubstituted aryl, or acid addition salt; n is an integer of 0 to 3; and m is an integer of 0 to 4.

Item 3. The fluorescent probe according to Item 2, wherein the compound is represented by Formula (1A):

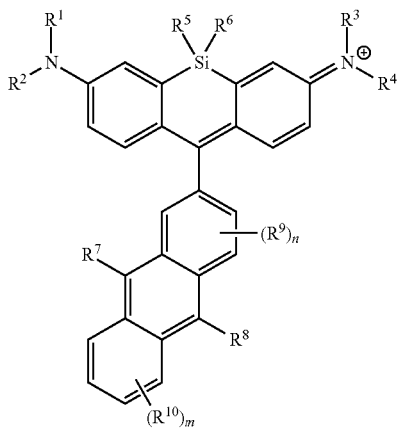

wherein $R^1$ to $R^{10}$, n, and m are as defined above.

Item 4. A singlet oxygen detection agent, comprising the fluorescent probe according to any one of Items 1 to 3.

Item 5. The singlet oxygen detection agent according to Item 4, wherein the singlet oxygen detection agent contains 10 to 500 nmol/L of the fluorescent probe.

Item 6. A method for detecting singlet oxygen generated in a cell, comprising the steps of:

(1) culturing a cell under a condition in which singlet oxygen is generated;

(2) preparing and culturing a mixed culture solution containing the culture solution obtained in step (1) and the fluorescent probe of any one of Items 1 to 3, wherein the concentration of the fluorescent probe is 10 to 500 nmol/L; and (3) irradiating the mixed culture solution obtained in step (2) with light.

Item 7. The method for detecting singlet oxygen according to Item 6, wherein the condition in which singlet oxygen is generated in step (1) is a condition having a photosensitizer.

Item 8. The method for detecting singlet oxygen according to Item 7, wherein the photosensitizer is protoporphyrin IX.

Item 9. The method for detecting singlet oxygen according to any one of Items 6 to 8, wherein the cell is a cancer cell.

Item 10. The method for detecting singlet oxygen according to any one of Items 6 to 9, wherein the method site-selectively detects singlet oxygen generated near a mitochondrial inner membrane in the cell.

Item 11. A compound represented by Formula (1):

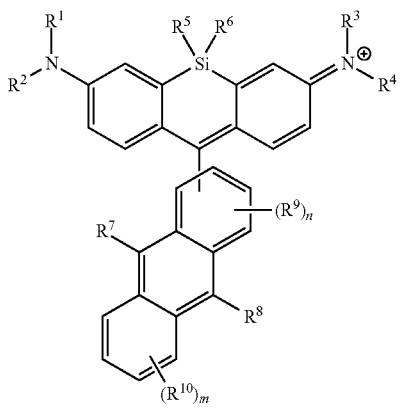

wherein $R^1$ to $R^4$ are the same or different, and each represents hydrogen, substituted or unsubstituted alkyl, substituted or unsubstituted alkenyl, substituted or unsubstituted alkynyl, or substituted or unsubstituted aryl; $R^5$ and $R^6$ are the same or different, and each represents hydrogen, hydroxy, halogen, substituted or unsubstituted alkyl, substituted or unsubstituted alkenyl, substituted or unsubstituted alkynyl, or substituted or unsubstituted aryl; $R^7$ and $R^8$ are the same or different, and each represents hydrogen, halogen, substituted or unsubstituted alkyl, substituted or unsubstituted alkenyl, substituted or unsubstituted alkynyl, substituted or unsubstituted aryl, substituted or unsubstituted alkoxy, or acid addition salt; $R^9$ and $R^{10}$ are the same or different, and each represents hydrogen, hydroxy, halogen, substituted or unsubstituted alkyl, substituted or unsubstituted alkenyl, substituted or unsubstituted alkynyl, substituted or unsubstituted aryl, or acid addition salt; n is an integer of 0 to 3; and m is an integer of 0 to 4.

Item 12. The compound according to Item 11, wherein the compound is represented by Formula (1A):

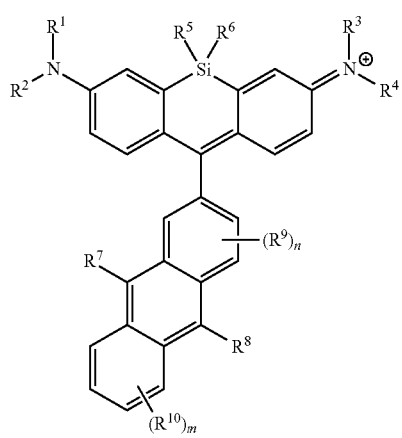

wherein $R^1$ to $R^{10}$, n, and m are as defined above.

Item 13. A cell assay reagent comprising the fluorescent probe of any one of Items 1 to 3, the singlet oxygen detection agent of Item 4 or 5, or the compound of Item 11 or 12.

Item 14. Use of the fluorescent probe of any one of Items 1 to 3, the singlet oxygen detection agent of Item 4 or 5, or the compound of Item 11 or 12 for detection of singlet oxygen.

Advantageous Effects of Invention

In the absence of singlet oxygen, the luminescence of the fluorescent probe of the present invention is suppressed; conversely, in the presence of singlet oxygen, the fluorescent probe of the present invention produces more intensive luminescence by the irradiation of a specific light (i.e., the fluorescence intensity greatly increases), thereby enabling the detection of singlet oxygen.

Further, since such luminescence (increased fluorescence intensity) is not observed in the presence of other reactive oxygen species, and is observed only in the presence of singlet oxygen, it is possible to selectively detect singlet oxygen among various reactive oxygen species.

Since the fluorescent probe of the present invention is excited and thereby produces luminescence by being irradiated with far red (low-energy light), it is possible to avoid the luminescence of the cell itself, thereby enabling more accurate detection of singlet oxygen, compared with the fluorescein chromophore used in previously known SOSG.

Since the singlet oxygen generation quantum yield of the fluorescent probe of the present invention is lower than that of the fluorescein chromophore used in the previously known SOSG, the drawback of giving erroneous fluorescent signals due to self-oxidation of the fluorescent probe can be prevented.

The fluorescent probe of the present invention more easily penetrates the cell; further, since the silicon-rhodamine skeleton has a net charge of +1 as well as appropriate lipophilicity, the fluorescent probe is accumulated in the mitochondrial inner membrane. Using the characteristics, it is also possible to perform site-selective color rendering (real-time visualization) of mitochondria using, as a photosensitizer, protoporphyrin IX (which hereinafter may also be referred to as "PpIX") biosynthesized in the mitochondria by 5-aminolevulinic acid.

DETAILED DESCRIPTION OF THE INVENTION

Figure 1:
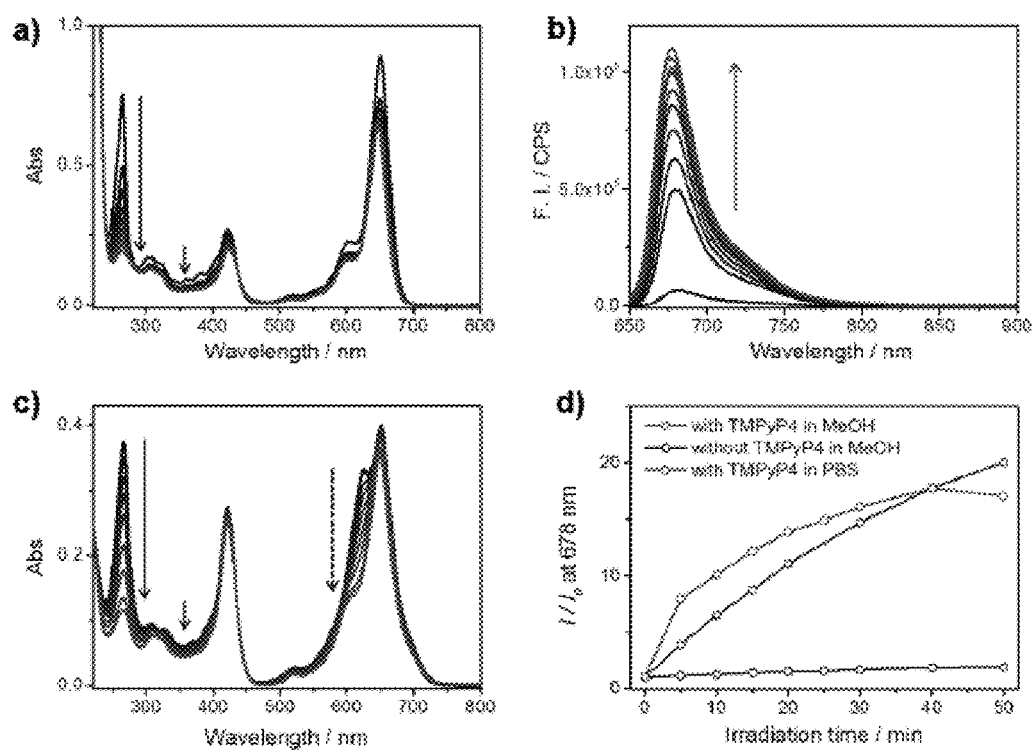
FIG. 1: Graphs showing fluorescence spectrum and temporal change in luminescence spectrum with respect to Si-DMA of Example 1 incubated together with $TMPyP_4$. Each graph shows the results of 50-minute light irradiation on Si-DMA dissolved in methanol (a) and b)) or a PBS solution (c)) together with $TMPyP_4$. d) shows the change in the fluorescence of Si-DMA over time.

1. Fluorescent Probe for Detecting Singlet Oxygen

The fluorescent probe for detecting singlet oxygen of the present invention comprises a compound having a silicon-rhodamine skeleton and a skeleton that increases the fluorescence of the fluorescent probe after trapping singlet oxygen to be greater than the fluorescence before trapping singlet oxygen, or a salt, hydrate, or solvate thereof. In particular, the fluorescent probe for detecting singlet oxygen of the present invention preferably consists only of a compound having a silicon-rhodamine skeleton and a skeleton that increases the fluorescence of the fluorescent probe after trapping singlet oxygen to be greater than the fluorescence before trapping singlet oxygen, or a salt, hydrate, or solvate thereof.

Since the fluorescent probe of the present invention has a silicon-rhodamine skeleton, it is selectively excited by red light excitation. On the other hand, since the fluorescent probe of the present invention has a skeleton (which hereinafter may also be referred to as "a specific skeleton") that increases the fluorescence of the fluorescent probe after trapping singlet oxygen to be greater than the fluorescence before trapping singlet oxygen, the excitation state of the selectively excited silicon rhodamine is cancelled, and the luminescence is suppressed (quenching effect). However, in the presence of singlet oxygen, the quenching effect is lost by the trapping of singlet oxygen by the specific skeleton (addition reaction of specific skeleton and singlet oxygen); thus excitation and luminescence by far-red are possible. Conversely, such a luminescence effect cannot be observed in the presence of other reactive oxygen species. Therefore, since excitation and luminescence are possible only in the presence of singlet oxygen, it is possible to selectively detect singlet oxygen.

Further, since the fluorescent probe of the present invention having such a structure is excited and produces luminescence by far red (low-energy light), it is possible to suppress the luminescence of the cell itself, thereby more accurately detecting singlet oxygen.

Since the singlet oxygen generation quantum yield of the fluorescent probe of the present invention is low, the drawback of giving erroneous fluorescent signals due to self-oxidation of the fluorescent probe can be prevented.

Moreover, the fluorescent probe of the present invention more easily penetrates the cell; in addition, since the silicon-rhodamine skeleton has a net charge of +1 as well as appropriate lipophilicity, the fluorescent probe is accumulated in the mitochondrial inner membrane. Using these characteristics, it is also possible to perform site-selective color rendering (real-time visualization) of mitochondria using, as a photosensitizer, protoporphyrin IX (which hereinafter may also be referred to as "PpIX") biosynthesized in the mitochondria by 5-aminolevulinic acid.

The "silicon-rhodamine skeleton" designates a skeleton in which the oxygen (O) of a rhodamine skeleton is replaced by a tetravalent silicon-containing group. With the silicon-rhodamine skeleton, the absorption spectrum and the luminescence spectrum are redshifted by about 100 nm or more, compared with general rhodamine dye. This solves the drawback of difficulty in observing the fluorescence of a dye due to the luminescence of the cell itself when short-wavelength light is used. Therefore, it is possible to more accurately detect singlet oxygen, thus inhibiting erroneous fluorescent signals. Further, it is also possible to perform site-selective color rendering (real-time visualization) of mitochondria using, as a photosensitizer, protoporphyrin IX (which hereinafter may also be referred to as "PpIX") biosynthesized in the mitochondria by 5-aminolevulinic acid.

The "skeleton that increases the fluorescence of the fluorescent probe after trapping singlet oxygen to be greater than the fluorescence before trapping singlet oxygen" (the specific skeleton mentioned above) is not particularly limited insofar as it is capable of quenching the fluorescence by the excitation of the silicon-rhodamine skeleton and trapping singlet oxygen. Examples include a naphthalene skeleton, an anthracene skeleton, a benzofuran skeleton, a cholesterol skeleton, and a tocopherol skeleton. However, an anthracene skeleton is preferable in terms of quenching fluorescence by excitation of the silicon-rhodamine skeleton, efficiency in trapping singlet oxygen, and better prevention of the quenching of fluorescence produced by the excitation of the silicon-rhodamine skeleton after trapping singlet oxygen.

The fluorescent probe satisfying such conditions preferably comprises a compound represented by Formula (1):

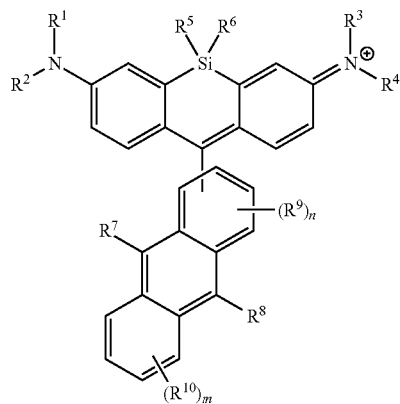

wherein $R^1$ to $R^4$ are the same or different, and each represents hydrogen, substituted or unsubstituted alkyl, substituted or unsubstituted alkenyl, substituted or unsubstituted alkynyl, or substituted or unsubstituted aryl; $R^5$ and $R^6$ are the same or different, and each represents hydrogen, hydroxy, halogen, substituted or unsubstituted alkyl, substituted or unsubstituted alkenyl, substituted or unsubstituted alkynyl, or substituted or unsubstituted aryl; $R^7$ and $R^8$ are the same or different, and each represents hydrogen, halogen, substituted or unsubstituted alkyl, substituted or unsubstituted alkenyl, substituted or unsubstituted alkynyl, substituted or unsubstituted aryl, substituted or unsubstituted alkoxy, or acid addition salt; $R^9$ and $R^{10}$ are the same or different, and each represents hydrogen, hydroxy, halogen, substituted or unsubstituted alkyl, substituted or unsubstituted alkenyl, substituted or unsubstituted alkynyl, substituted or unsubstituted aryl, or acid addition salt; n is an integer of 0 to 3; and m is an integer of 0 to 4, or a salt, hydrate, or solvate thereof, and more preferably comprises a compound represented by Formula (1A):

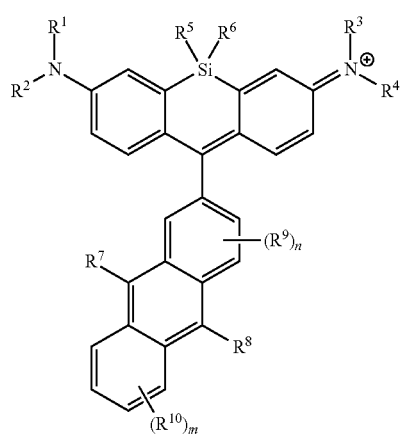

wherein $R^1$ to $R^{10}$, n, and m are as defined above, or a salt, hydrate, or solvate thereof. In particular, the probe preferably consists only of the compound represented by General Formula (1), or a salt, hydrate, or solvate thereof. The probe more preferably consists only of the compound represented by Formula (1A), or a salt, hydrate, or solvate thereof. These compounds represented by Formulas (1) and (1A) are novel compounds that have not been disclosed in any documents.

In Formulas (1) and (1A), alkyl represented by $R^1$ to $R^4$ may be any of linear alkyl, branched alkyl, and cyclic alkyl.

The linear alkyl is preferably $C_{1-6}$ (in particular $C_{1-4}$) linear alkyl. Examples include methyl, ethyl, n-propyl, n-butyl, n-pentyl, and n-hexyl.

The branched alkyl is preferably $C_{3-6}$ (in particular $C_{3-5}$) branched alkyl. Examples include isopropyl, isobutyl, tert-butyl, sec-butyl, neopentyl, isohexyl, and 3-methylpentyl.

The cyclic alkyl is preferably $C_{3-10}$ (in particular $C_{3-7}$) cyclic alkyl. Examples include cyclopropyl, cyclopentyl, cyclohexyl, and cycloheptyl.

Examples of the optional substituents of alkyl represented by $R^1$ to $R^4$ include, but are not particularly limited to, halogen (fluorine, chlorine, bromine, iodine, or the like), hydroxy, acid addition salts (such as hydrochloride, sulfate, nitrate and like mineral acid salts; and p-toluenesulfonate, methanesulfonate, maleate, oxalate and like organic acid salts). The number of substituents is not particularly limited; however, 0 to 6 substituents are preferable, and 0 to 3 substituents are more preferable.

The alkenyl represented by $R^1$ to $R^4$ in Formulas (1) and (1A) is preferably a $C_{2-6}$ (in particular $C_{2-4}$) alkenyl. Examples include vinyl, allyl, and isopropenyl.

Examples of the optional substituents of alkenyl represented by $R^1$ to $R^4$ include, but are not particularly limited to, halogen (fluorine, chlorine, bromine, iodine, or the like), hydroxy, acid addition salts (such as hydrochloride, sulfate, nitrate and like mineral acid salts; and p-toluenesulfonate, methanesulfonate, maleate, oxalate and like organic acid salts). The number of substituents is not particularly limited; however, 0 to 6 substituents are preferable, and 0 to 3 substituents are more preferable.

The alkynyl represented by $R^1$ to $R^4$ in Formulas (1) and (1A) is preferably a $C_{2-6}$ (in particular $C_{2-4}$) alkynyl. Examples include ethynyl, propynyl, and isopropynyl.

Examples of the optional substituents of alkynyl represented by $R^1$ to $R^4$ include, but are not particularly limited to, halogen (fluorine, chlorine, bromine, iodine, or the like), hydroxy, acid addition salts (such as hydrochloride, sulfate, nitrate and like mineral acid salts; and p-toluenesulfonate, methanesulfonate, maleate, oxalate and like organic acid salts). The number of substituents is not particularly limited; however, 0 to 6 substituents are preferable, and 0 to 3 substituents are more preferable.

The aryl represented by $R^1$ to $R^4$ in Formulas (1) and (1A) may be monocyclic aryl or condensed-ring aryl. Examples include phenyl, oligo aryl (such as naphthyl or anthryl), biphenyl, terphenyl, pyrenyl, phenanthrenyl, and fluorenyl.

Examples of the optional substituents of aryl represented by $R^1$ to $R^4$ include, but are not particularly limited to, halogen (fluorine, chlorine, bromine, iodine, or the like), hydroxy, acid addition salts (such as hydrochloride, sulfate, nitrate and like mineral acid salts; and p-toluenesulfonate, methanesulfonate, maleate, oxalate and like organic acid salts). The number of substituents is not particularly limited; however, 0 to 6 substituents are preferable, and 0 to 3 substituents are more preferable.

$R^1$ to $R^4$ may be the same or different, but are preferably the same from an economic standpoint. Further, among the above examples, in terms of, for example, the fluorescence produced by the excitation of silicon-rhodamine skeleton, $R^1$ to $R^4$ are preferably alkyl, more preferably linear alkyl, further preferably $C_{1-6}$ linear alkyl, particularly preferably $C_{1-4}$ linear alkyl, and most preferably methyl.

Examples of halogen represented by $R^5$ and $R^6$ in Formulas (1) and (1A) include fluorine, chlorine, bromine, and iodine.

Examples of alkyl, alkenyl, alkynyl and aryl represented by $R^5$ and $R^6$ in Formulas (1) and (1A) include the same groups exemplified above. Further, examples of the optional substituents of alkyl, alkenyl, alkynyl and aryl represented by $R^5$ and $R^6$ include the same substituents exemplified above, and the number of substituents is also similar to the above.

$R^5$ and $R^6$ may be the same or different, but are preferably the same from an economic standpoint. Further, among the above examples, in terms of, for example, the fluorescence produced by the excitation of a silicon-rhodamine skeleton, $R^5$ and $R^6$ are preferably alkyl, more preferably linear alkyl, further preferably $C_{1-6}$ linear alkyl, particularly preferably $C_{1-4}$ linear alkyl, and most preferably methyl.

Examples of alkyl, alkenyl, alkynyl and aryl represented by $R^7$ and $R^8$ in Formulas (1) and (1A) include the same groups exemplified above. Further, examples of the optional substituents of alkyl, alkenyl, alkynyl and aryl represented by $R^7$ and $R^8$ include the same substituents exemplified above, and the number of substituents is also similar to the above.

In Formulas (1) and (1A), alkoxy represented by $R^7$ and $R^8$ is preferably $C_{1-6}$ (in particular $C_{1-4}$) alkoxy. Examples include methoxy, ethoxy, n-propoxy, isopropoxy, n-butoxy, isobutoxy, tert-butoxy, and sec-butoxy.

Examples of the optional substituents of alkoxy represented by $R^7$ and $R^8$ include, but are not particularly limited to, halogen (fluorine, chlorine, bromine, iodine, or the like), hydroxy, acid addition salts (such as hydrochloride, sulfate, nitrate and like mineral acid salts; and p-toluenesulfonate, methanesulfonate, maleate, oxalate and like organic acid salts). The number of substituents is not particularly limited; however, 0 to 6 substituents are preferable, and 0 to 3 substituents are more preferable.

Examples of the acid addition salt represented by $R^7$ and $R^8$ in Formulas (1) and (1A) include hydrochloride, sulfate, nitrate and like mineral acid salts; and p-toluenesulfonate, methanesulfonate, maleate, oxalate and like organic acid salts.

$R^7$ and $R^8$ may be the same or different, but are preferably the same from an economic standpoint. Further, among the above examples, in terms of, for example, quenching the fluorescence produced by the excitation of silicon-rhodamine skeleton, singlet oxygen trapping efficiency, and better prevention of quenching of fluorescence produced by the excitation of the silicon-rhodamine skeleton after trapping singlet oxygen, $R^7$ and $R^8$ are preferably alkyl, more preferably linear alkyl, further preferably $C_{1-6}$ linear alkyl, particularly preferably $C_{1-4}$ linear alkyl, and most preferably methyl.

Examples of alkyl, alkenyl, alkynyl and aryl represented by $R^9$ and $R^{10}$ in Formulas (1) and (1A) include the same groups exemplified above. Further, examples of the optional substituents of alkyl, alkenyl, alkynyl and aryl represented by $R^9$ and $R^{10}$ include the same substituents exemplified above, and the number of substituents is also similar to the above.

$R^9$ and $R^{10}$ may be the same or different, but are preferably the same from an economic standpoint. Further, among the above examples, in terms of, for example, quenching the fluorescence produced by the excitation of the silicon-rhodamine skeleton, singlet oxygen trapping efficiency, and better prevention of quenching of fluorescence produced by the excitation of the silicon-rhodamine skeleton after trapping singlet oxygen, $R^9$ and $R^{10}$ are preferably hydrogen.

In Formulas (1) and (1A), n as the number of substitutions of $R^9$ is an integer of 0 to 3. In terms of, for example, quenching the fluorescence produced by the excitation of the silicon-rhodamine skeleton, singlet oxygen trapping efficiency, and better prevention of quenching of fluorescence produced by the excitation of the silicon-rhodamine skeleton after trapping singlet oxygen, n is preferably an integer of 0 to 2, and more preferably 0 or 1.

In Formulas (1) and (1A), m as the number of substitutions of $R^{10}$ is an integer of 0 to 4. In terms of, for example, quenching the fluorescence produced by the excitation of the silicon-rhodamine skeleton, singlet oxygen trapping efficiency, and better prevention of quenching of fluorescence produced by the excitation of the silicon-rhodamine skeleton after trapping singlet oxygen, m is preferably an integer of 0 to 3, and more preferably 0 to 2.

The fluorescent probe of the present invention satisfying such conditions is not particularly limited; however, the fluorescent probe of the present invention preferably comprises the compound represented by Formula (1A1):

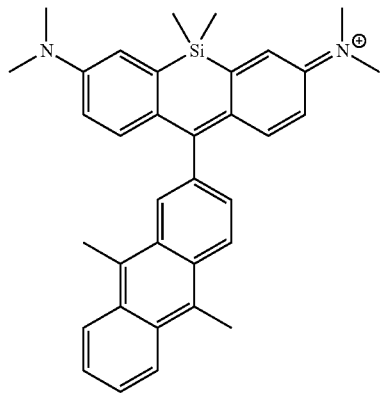

or a salt, hydrate, or solvate thereof, and more preferably consists only of the compound represented by Formula (1A1), or a salt, hydrate, or solvate thereof.

In the fluorescent probe of the present invention, the silicon-rhodamine skeleton may have a suitable counterion (anion). Examples of counterion include, but are not limited to, halogen ion (such as fluorine ion, chlorine ion, bromine ion, or iodine ion), cyan ion, acetic acid ion, and trifluoroacetic acid ion.

The fluorescent probe of the present invention may be present in the form of a salt. Examples of base addition salts include sodium salts, potassium salts, calcium salts, magnesium salts and like metal salts; ammonium salts; trimethylamine salts and like organic amine salts. Examples of acid addition salts include hydrochloride, sulfate, nitrate and like mineral acid salts; and p-toluenesulfonate, methanesulfonate, maleate, oxalate and like organic acid salts. In addition, a salt with an amino acid, such as glycine, may also be formed.

Further, the fluorescent probe of the present invention may be present as a hydrate or a solvate. These substances are also encompassed in the scope of the present invention.

2. Method for Producing Fluorescent Probe

The method for producing the fluorescent probe of the present invention is not particularly limited; however, the fluorescent probe of the present invention is obtained, for example, by reacting a silicon-xanthone compound or a derivative thereof with a compound having the above specific skeleton substituted with halogen.

A method for producing the compound group represented by General Formula (1) is shown below as an example of the method for producing the fluorescent probe of the present invention. A similar method is used for producing compound groups of the fluorescent probe of the present invention other than the compound group represented by General Formula (1), except that a different material is used.

The compound group represented by General Formula (1) may be produced by reacting the silicon-xanthone compound represented by Formula (2):

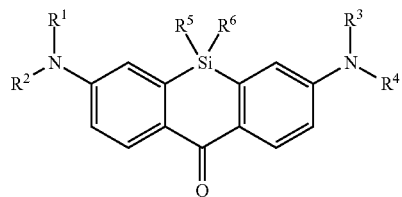

wherein $R^1$ to $R^6$ are as defined above, with the anthracene compound represented by Formula (3):

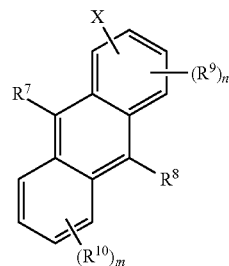

wherein $R^7$ to $R^{10}$, n and m are as defined above; and X is halogen, in the presence of a base.

In Formula (2), $R^1$ to $R^6$ are as defined above. More specifically, examples of the silicon-xanthone compound represented by Formula (2) include:

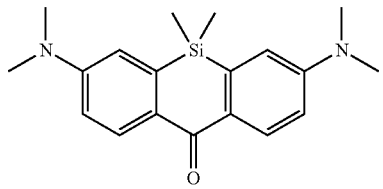

The silicon-xanthone compound represented by Formula (2) may be a known or commercially-available compound, or may be synthesized. The compound represented by Formula (2) may be synthesized, for example, according to the method disclosed in Lukinavicios, G. et al., Nat. Chem., 5, 132-139 (2013), Nagano T. et al., ACS Chem. Biol. 6, 600-608 (2011) or a similar method.

In Formula (3), $R^7$ to $R^{10}$, n and m are as defined above. Further, examples of halogen represented by X in Formula (3) include fluorine, chlorine, bromine, and iodine. The halogen is preferably chlorine or bromine, and more preferably bromine.

More specifically, examples of the anthracene compound represented by Formula (3) include:

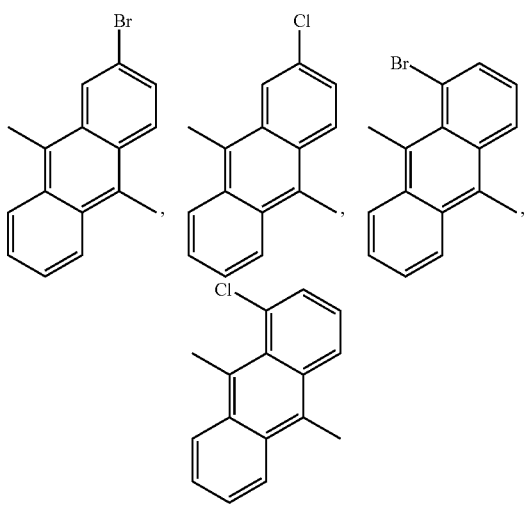

The anthracene compound represented by Formula (3) may be a known or commercially-available compound, or may be synthesized. The compound represented by Formula (3) may be synthesized, for example, according to the method disclosed in Keana, J. F. W. et al., J. Org. Chem., 51, 3456-3462 (1986) or a similar method.

In terms of the yield, the amount of silicon-xanthone compound represented by Formula (2) is preferably set to an excessive amount relative to the anthracene compound represented by Formula (3). Specifically, the amount of anthracene compound represented by Formula (3) is generally preferably about 0.02 to 1 mol, more preferably about 0.03 to 0.3 mol, and further preferably about 0.05 to 0.2 mol, per mol of the silicon-xanthone compound represented by Formula (2).

Examples of the base include methyllithium, ethyllithium, n-butyllithium, s-butyllithium, t-butyllithium and like alkyl lithium; phenyl lithium and like aryl lithium; and Grignard reaction agent. In terms of the yield, the base is preferably alkyl lithium, more preferably n-butyllithium, s-butyllithium, or the like, and further preferably s-butyllithium.

In the present invention, although the base may be added simultaneously with the silicon-xanthone compound represented by Formula (2) and the anthracene compound represented by Formula (3), it is also possible to mix the anthracene compound represented by Formula (3) with the base, and then mix the resulting mixture with the silicon-xanthone compound represented by Formula (2). The latter is preferable in terms of the yield.

The amount of the base is, in terms of the yield, generally preferably about 0.1 to 10 mol, more preferably about 0.3 to 3 mol, and further preferably about 0.5 to 2 mol, per mol of the xanthone compound represented by Formula (2).

When a salt of the compound represented by General Formula (1) explained above is synthesized as the fluorescent probe of the present invention, it is preferable to add a salt corresponding to the salt to be obtained upon the reaction of the xanthone compound represented by Formula (2) and the anthracene compound represented by Formula (3).

Generally, this reaction may be performed in a solvent. The solvent may be a single solvent or a combination of two or more. In the present invention, cyclic ethers are preferable, and tetrahydrofuran is particularly preferable.

The reaction temperature is not particularly limited; however, in terms of the yield, the reaction temperature is preferably about −150 to 100° C., and more preferably about −100 to 50° C. Further, the reaction time is also not particularly limited insofar as the reaction can be sufficiently performed; however, the reaction time is preferably 1 to 48 hours, and more preferably 2 to 24 hours.

When the anthracene compound represented by Formula (3) and a base are mixed first, and then the resulting mixture and the silicon-xanthone compound represented by Formula (2) are mixed, it is possible to react the anthracene compound represented by Formula (3) with a base at about −150 to 0° C. (in particular about −100 to −50° C.) for about 1 to 120 minutes (in particular about 30 to 60 minutes), and then react the resulting reaction mixture with the silicon-xanthone compound represented by Formula (2) at about 0 to 100° C. (in particular about 20 to 50° C.) for about 1 to 48 hours (in particular about 2 to 24 hours).

Further, the reaction is preferably performed in an inert gas atmosphere (such as nitrogen gas or argon gas).

After the reaction is completed, general isolation and purification step are performed, thereby yielding the fluorescent probe of the present invention made from the compound represented by Formula (1).

3. Singlet Oxygen Detection Agent

As described above, the fluorescent probe for detecting singlet oxygen of the present invention does not produce fluorescence (light) before trapping singlet oxygen, and produces fluorescence (light) in response to specific light after trapping singlet oxygen. Conversely, the fluorescent probe for detecting singlet oxygen of the present invention does not show such a behavior in the presence of other reactive oxygen species, i.e., it does not produce fluorescence (light).

As is clear from the above, since the fluorescent probe for detecting singlet oxygen of the present invention has such an idiosyncratic property, i.e., it produces fluorescence (light) by irradiation of specific light only in the presence of singlet oxygen among various reactive oxygen species, the probe can be suitably used for a singlet oxygen detection agent.

Using the fluorescent probe for detecting singlet oxygen of the present invention enables excitation and luminescence by irradiation of far red (low-energy light), thereby inhibiting luminescence of the cell itself. Further, since the singlet oxygen generation quantum yield of the fluorescent probe for detecting singlet oxygen of the present invention is low, the drawback of giving erroneous fluorescent signals due to self-oxidation of the fluorescent probe can be inhibited, thereby more accurately detecting singlet oxygen generated in the cell.

Furthermore, the fluorescent probe of the present invention more easily penetrates the cell; further, since the silicon-rhodamine skeleton has a net charge of +1 and appropriate lipophilicity, the fluorescent probe is accumulated in the mitochondrial inner membrane. Using these characteristics, it is also possible to perform site-selective color rendering (real-time visualization) of mitochondria using, as a photosensitizer, protoporphyrin IX (which hereinafter may also be referred to as "PpIX") biosynthesized in the mitochondria by 5-aminolevulinic acid. Therefore, the fluorescent probe of the present invention is particularly useful as an agent for detecting singlet oxygen generated near the mitochondrial inner membrane.

The singlet oxygen detection agent of the present invention comprises the fluorescent probe for detecting singlet oxygen of the present invention. The singlet oxygen detection agent of the present invention is preferably in the form of a solution in which the fluorescent probe is dissolved in an organic solvent. In terms of further ensuring singlet oxygen detection and site-selective color rendering (real-time visualization) of mitochondria, as well as further inhibiting erroneous fluorescent signals due to self-oxidation of the fluorescent probe, the content of the fluorescent probe for detecting singlet oxygen of the present invention is preferably 10 to 500 nmol/L, and more preferably 20 to 100 nmol/L.

When the singlet oxygen detection agent of the present invention is made into a solution containing the fluorescent probe for detecting singlet oxygen of the present invention, examples of usable organic solvents include, but are not particularly limited to, polar solvents and nonpolar solvents.

Examples of polar solvents include ether compounds (such as tetrahydrofuran (THF), anisole, 1,4-dioxane, or cyclopentyl methyl ether), alcohols (such as methanol, ethanol, or allyl alcohol), ester compounds (such as ethyl acetate), ketones (such as acetone), halogenated hydrocarbons (such as dichloromethane or chloroform), dimethyl sulfoxide (DMSO), amide-based solvents (such as N,N-dimethyl formamide (DMF), dimethylacetamide (DMA), 1,3-dimethyl-2-imidazolidinone (DMI), or N-methylpyrrolidone (NMP)).

Examples of nonpolar solvents include pentane, hexane, cyclohexane, heptane and like aliphatic organic solvents; and benzene, toluene, xylene, mesitylene and like aromatic solvents.

Of these, in terms of further decreasing the fluorescence in the absence of singlet oxygen and inhibiting the drawback of giving erroneous fluorescent signals, polar solvents are preferable. Alcohols, ketones, halogenated hydrocarbons, dimethyl sulfoxide, and the like are more preferable, and methanol, acetone, chloroform, dimethyl sulfoxide, and the like are further preferable.

As mentioned above, the singlet oxygen detection agent of the present invention is preferably in the form of a solution. In view of introducing the agent into cells (in particular, into mitochondria), the pH is preferably about 3.0 to 9.0, and more preferably about 6.0 to 8.0. To adjust the pH of the singlet oxygen detection agent of the present invention, buffers (such as HEPES buffer, tris buffer, tricine-sodium hydroxide buffer, phosphate buffer, or phosphate buffered saline), and the like may be used.

4. Singlet Oxygen Detection Method

In the present invention, the method for detecting singlet oxygen is not particularly limited; however, the method preferably comprises the steps of:

(1) culturing a cell under a condition in which singlet oxygen is generated;
(2) preparing and culturing a mixed culture solution containing the culture solution obtained in step (1) and the fluorescent probe of the present invention, wherein the concentration of the fluorescent probe is 10 to 500 nmol/L; and
(3) irradiating the mixed culture solution obtained in step (2) with light.

Step (1)

In step (1), firstly, desired cells are cultured under a condition in which singlet oxygen is generated.

The cells are not particularly limited; however, in terms of medical usability and the like, cancer cells (Hela cells, CHO cells), RAW265.7 macrophage and the like are preferable.

In step (1), the condition in which singlet oxygen is generated is not particularly limited and any condition in which singlet oxygen can be generated may be used; however, it is preferable to use a cell culture solution containing a photosensitizer.

Examples of the photosensitizer used in the step include, but are not particularly limited to, protoporphyrin IX (biosynthesized in the mitochondria by 5-aminolevulinic acid; which hereinafter may also be referred to as "PpIX"), tetra-(N-methyl-4-pyridyl)porphyrin (localized in the lysosome; which hereinafter may also be referred to as "TMPyP4"), and a photosensitizing protein Killer Red (expressed in the mitochondria). However, in terms of coexistence with the fluorescent probe in the space, mass generation of singlet oxygen, and acute cell characteristics, protoporphyrin IX is preferable.

The content of the photosensitizer in the cell culture solution is not particularly limited; however, in terms of performing more accurate color rendering of mitochondrial inner membrane and preventing erroneous fluorescent signals, as well as producing fluorescence (light) for a prolonged period of time, the content is preferably 50 to 250 µg/mL, and more preferably 100 to 200 µg/mL.

In step (1), fetal bovine serum (FBS) may be added to the cell culture solution so as to more appropriately culture the target cells. Further, in order to adjust the pH of the cell culture solution to about 6.0 to 8.0, buffers (such as HEPES buffer, tris buffer, tricine-sodium hydroxide buffer, phosphate buffer, or phosphate buffered saline) and the like may be used.

In step (1), the culture time is not particularly limited insofar as the desired cells are sufficiently cultured; however, the culture time is preferably 1 to 72 hours, and more preferably 2 to 48 hours.

Step (2)

In step (2), it is preferable to add the fluorescent probe of the present invention to the culture solution obtained in step (1). In this step, the amount of the fluorescent probe of the present invention is preferably adjusted so that the concentration of the fluorescent probe is about 10 to 500 nmol/L (in particular, about 20 to 100 nmol/L) in the resulting mixed culture solution. In this step, to adjust the pH of the mixed culture solution to about 6.0 to 8.0, buffers (such as HEPES buffer, tris buffer, tricine-sodium hydroxide buffer, phosphate buffer, or phosphate buffered saline) and the like may be used.

Step (3)

In step (3), the mixed culture solution obtained in step (2) is subjected to light irradiation.

The wavelength of the light irradiation is not particularly limited; however, in view of the exhibition of fluorescence (luminescence) of the fluorescent probe of the present invention in response to far-red light or red light, as well as performing more accurate color rendering of the mitochondrial inner membrane and preventing erroneous fluorescent signals, the wavelength is preferably 500 to 800 nm, more preferably 600 to 750 nm, and further preferably 630 to 700 nm. More specifically, it is preferable to emit a visible ray having a wavelength within the above range.

Further, although the intensity of light irradiation is not particularly limited, in terms of preventing acute cytotoxicity or cell death caused by light irradiation, or preventing erroneous fluorescent signals due to optical color fading of the photosensitizer and the fluorescent probe, the intensity is preferably 0.01 to 100 $W/cm^2$, more preferably 0.1 to 10 $W/cm^2$, and further preferably 0.3 to 1 $W/cm^2$.

Further, although the duration of light irradiation is not particularly limited, in terms of preventing acute cytotoxicity or cell death caused by light irradiation, or preventing erroneous fluorescent signals due to optical color fading of the photosensitizer and the fluorescent probe, the duration is preferably 1 second to 60 minutes, more preferably 5 seconds to 5 minutes, and further preferably 10 seconds to 3 minutes.

5. Use

As stated above, the fluorescent probe for detecting singlet oxygen of the present invention is used to selectively detect singlet oxygen. The fluorescent probe for detecting singlet oxygen of the present invention is particularly capable of site-selectively detecting singlet oxygen generated near the mitochondrial inner membrane. This capability is also due to the fact that the diameter of mitochondria is generally about 200 to 400 nm and is similar to the diffusible distance of singlet oxygen in water, which is about 300 nm. Using this mechanism, for example, by modifying the fluorescent probe of the present invention with a morpholine derivative widely known as a lysosome marker or a functional group capable of labeling a specific intracellular protein, space-selective detection to the extent of the optical space resolution limit (about several hundred nm) with respect to singlet oxygen generated in a specific subcellular organelle (such as mitochondria) and in the vicinity of protein can be expected.

Further, in actual medical practice, the fluorescent probe for detecting singlet oxygen of the present invention is particularly useful for confirming the proper introduction of a photosensitizer into mitochondria, which is a major target organelle of PDT.

Furthermore, as stated above, since the fluorescent probe for detecting singlet oxygen of the present invention and the singlet oxygen detection agent of the present invention are capable of selectively detecting singlet oxygen, they are suitably used for evaluations of the oxidative stress alleviation effects of a test sample using cells on the skin or the like, evaluations of the antioxidant effects of a test sample on the skin or the like, evaluations of the singlet oxygen removing performance by the intake of a test sample, and various other evaluations. For example, it is known that irradiation of ultraviolet or blue light on the skin of an organism generates singlet oxygen, and changes the skin condition. More specifically, the fluorescent probe for detecting singlet oxygen of the present invention and the singlet oxygen detection agent of the present invention are useful in the evaluation of the influences of ultraviolet and blue light on the skin in the fields of cosmetics, health food, medicine and the like. Further, through these evaluations, the fluorescent probe for detecting singlet oxygen of the present invention and the singlet oxygen detection agent of the present invention may be effectively used for the prevention and treatment of inflammation, atopic dermatitis, skin lesions such as cancer, skin aging such as spots and wrinkles, and the like, which are induced by reactive oxygen, typically by singlet oxygen.

Examples

EXAMPLES

The present invention is more specifically explained below with reference to Examples; however, the present invention is not limited to these Examples.

The chemical reagents and solvents used in the Examples below were purchased from Sigma-Aldrich Chemical, Tokyo Chemical Industry Co., Ltd., Nacalai Tesque, Inc., and Wako Pure Chemical Industries, Ltd., and were used without being purified.

Further, the characteristics of the compounds (Si-DMA) obtained in the Examples were confirmed by measuring the $^1$H-NMR spectrum and high-resolution mass spectrum (HRMS) using JEOL ESC400 (400 MHz) and an electrospray-ionized (ESI) LTQ Orbitrap XL hybrid ion trap-Orbitrap mass spectrometer. Further, the NMR chemical shift, J-value and integral value were calculated using Delta Ver. 5 software (JEOL).

Further, in the in vitro measurement, unless otherwise specified, all bulk spectrum measurements were performed in a phosphate buffered saline (PBS) having a pH of 7.5 without Ca and Mg or spectral grade methanol. The absorption spectrum and fluorescence spectrum in the ground state were measured using the Shimadzu UV-3100 and Horiba FluoroMax-4, respectively. The bulk irradiation was performed using a xenon light source (LAX-C100, Asahi Spectra Co., Ltd.) and a wavelength filter (BA510-550, Olympus Corporation).

Protocol of Color Staining (PpIX and TMPyP$_4$)

A treatment requiring incubation of less than two hours was performed using a serum-free culture medium containing 20 mM of HEPES, and a treatment requiring incubation of four hours or more was performed using a blood serum-containing medium containing 20 mM of HEPES so as to maintain the cell viability. To label mitochondria, Mito Tracker® Green FM was diluted to 50 nM, and incubated for 30 minutes. Further, 10000 MW of dextran (A488- and A647-dextran) labeled with Alexa Fluor® 488 or Alexa Fluor® 647 was diluted to 50 µg/mL, and incubated for 24 hours, thereby staining lysosome.

Subsequently, a quick protocol provided by Molecular Probe® for introducing CellROX Green was followed. Using diluted Si-DMA and Si-Me, incubation was performed for 30 minutes to two hours by an experiment. To introduce a photosensitizer, 150 µg/mL of 5-aminolevulinic acid (5-ALA) or 10 LM TMPyP$_4$ were incubated for four hours and 24 hours, respectively. As a result, as previously reported, the conversion of 5-ALA into protoporphyrin IX (PpIX) in the mitochondria was confirmed by the fluorescence luminescence of PpIX.

Expression of KillerRed

A KillerRed vector was expressed in accordance with a general Lipofectamine® 2000 (Invitrogen) protocol. More specifically, $2 \times 10^5$ Hela cells were subcultured in a 35-mm glass bottom dish. The cells reached about 50% confluent in the next day.

Subsequently, a mixed solution of Lipofectamine reagent and DNA vector was obtained by mixing 6 µL Lipofectamine® 2000 with 7 µL pKillerRed-dMitovector (0.5 g/mL, Evrogen, catalog No. FP964) in an Opti-MEM solution (Gibco). Thereafter, the resulting solution was incubated for 20 minutes at room temperature. 300 µL of the mixed solution was added to a growth medium, and incubated for 24 hours. The expression of KillerRed was confirmed by monitoring KillerRed fluorescence using a wide-view microscope.

Cell and Cell Culture

HeLa cells and RAW264.7 macrophage were respectively obtained from Riken BioResource Center and Professor Nishi from the Institute of Scientific and Industrial Research, Osaka University. Unless otherwise specified, HeLa cells were used in the cell experiments of the present invention. HeLa cells and RAW264.7 macrophage were cultured at 37° C. using Dulbecco's modified eagle medium (D6429, Sigma) in which 10% fetal bovine serum (10099-141, Gibco) was added in a humidified incubator at 5% $CO_2$.

Example 1

Fluorescent Probe of the Present Invention (Si-DMA)

Silicon-Xanthone

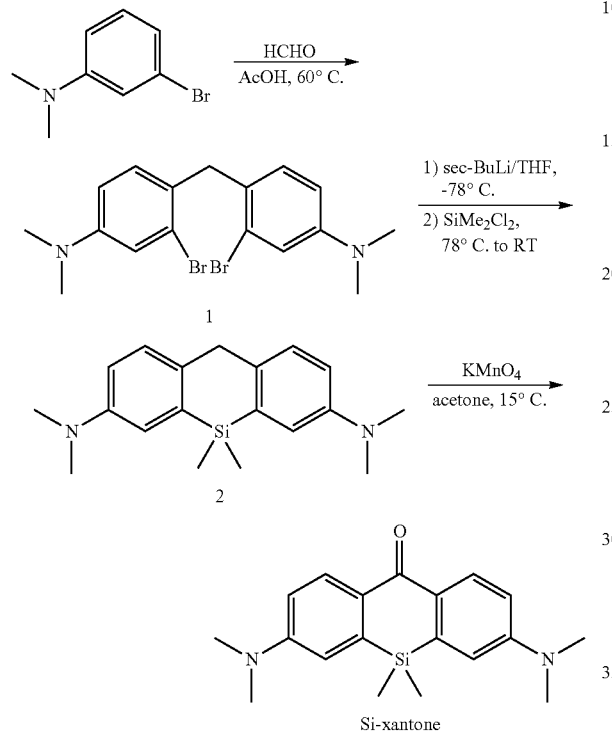

According to the method disclosed in Lukinavicios, G. et al., Nat. Chem., 5, 132-139 (2013), and Nagano T. et al., ACS Chem. Biol. 6, 600-608 (2011), silicon-xanthone (Si-xanthone) was synthesized using the synthesis route shown above.

2-Bromo-9,10-Dimethyl Anthracene (4)

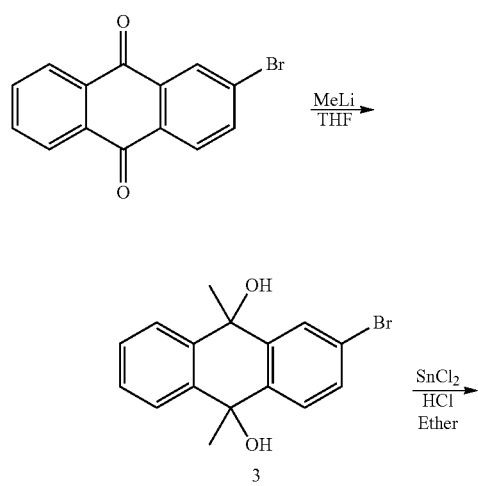

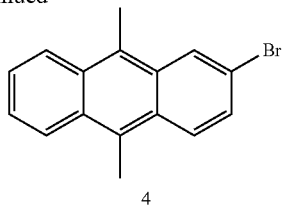

According to the method disclosed in Keana, J.F.W. et al., J. Org. Chem., 51, 3456-3462 (1986), 2-bromo-9,10-dimethyl anthracene (4) was synthesized using the synthesis route shown above.

Si-DMA

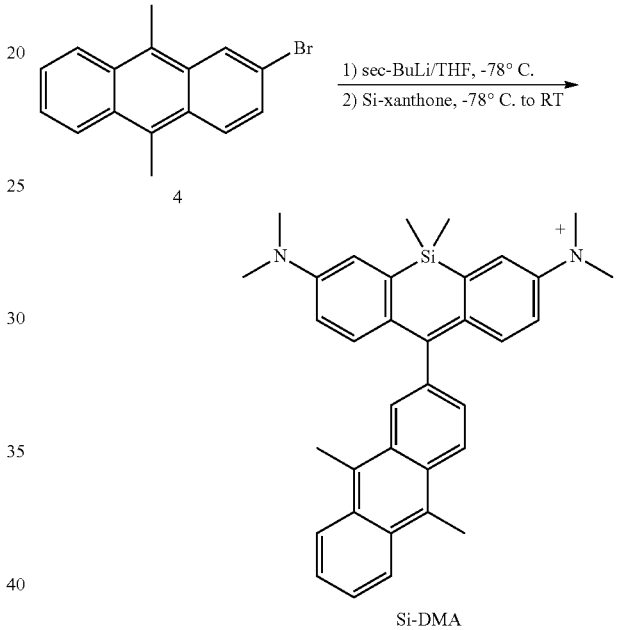

A dried flask was washed with argon, and 2-bromo-9,10-dimethyl anthracene (4) (0.85 mmol, 250 mg) and anhydrous THF (8.5 mL) were added to obtain a solution. The solution was cooled to −78° C., and sec-butyllithium (1.4 M cyclohexane solution, 0.61 mL, 0.85 mmol) was added, followed by stirring for 30 minutes.

Silicon-xanthone (Si-xanthone) (17.0 mg, 0.052 mmol) was dissolved in anhydrous THF (8.5 mL) at the same temperature, and slowly added to the solution obtained above. Thereafter, the mixture was heated to room temperature, and stirred overnight under argon atmosphere. 2N HCl was added to the solution to quench the reaction. The color of the solution changed from yellow to bluish green. Thereafter, the solution was stirred for 10 minutes at room temperature. Saturated $NaHCO_3$ was added to the solution, and the mixture was extracted using $CH_2Cl_2$. The organic layer was evaporated by drying using $Na_2SO_4$. The obtained residue was purified twice by gradient column chromatography (silica gel, $CH_2Cl_2$:methanol=1:0 to 4:1) and gel permeation chromatography, thereby obtaining the target product Si-DMA as a blue solid (5 mg, 18.7%). The obtained Si-DMA was stored in a −20° C. dimethyl sulfoxide (DMSO) in a dark room.

$^1$H-NMR (400 MHz, CD$_3$OD) δ: 0.65 (s, 6H), 3.05 (s, 3H), 3.18 (s, 3H), 6.74 (dd, 2H, J=9.6, 2.3 Hz), 7.27 (d, 2H, J=9.6 Hz), 7.39 (d, 2H, J=2.3 Hz), 7.44 (d, 1H, J=8.2 Hz), 7.59-7.61 (m, 2H), 8.24 (s, 1H), 8.39-8.46 (m, 2H), 8.55 (d, 1H, 8.7 Hz). HRMS (ESI)=m/z calculated for C$_{35}$H$_{37}$N$_2$Si 513.2721; found 513.2724.

When singlet oxygen is trapped in the thus-obtained Si-DMA, the anthracene structure collapses, thereby forming Si-DMEP, as shown in the reaction formula below:

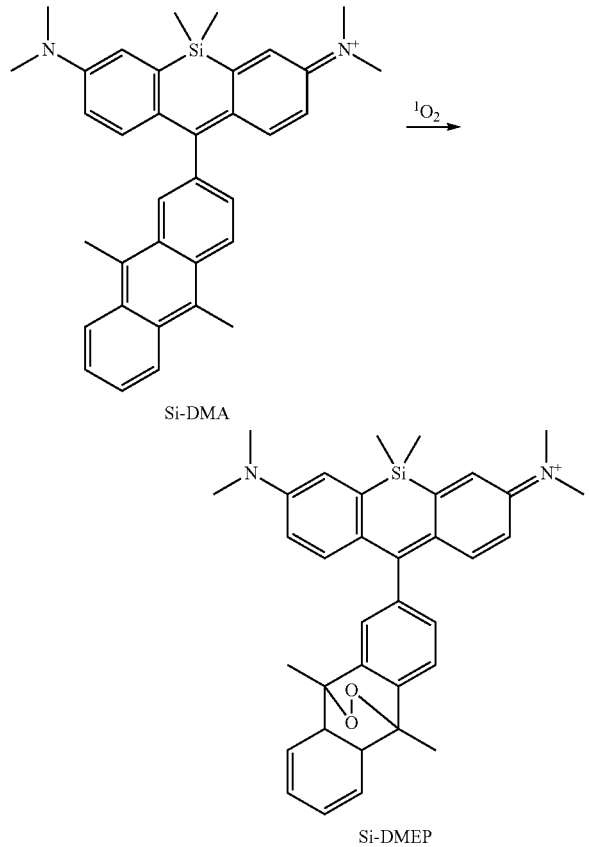

Comparative Example 1

Fluorescent Probe for Comparison (Si-Me)

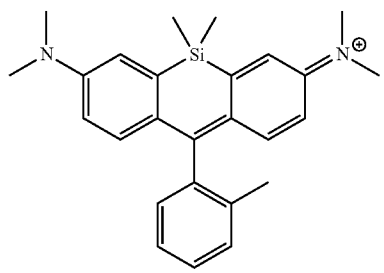

Silicon-rhodamine (Si-Me) substituted with 2 methyl benzene was synthesized according to the method disclosed in Nagano, T. et al., ACS Chem. Biol. 6, 600 (2011). The obtained Si-Me was stored in −20° C. dimethyl sulfoxide (DMSO) in a dark room.

Experiment 1

Fluorescence Spectrum and Luminescence Spectrum

FIG. 1 shows temporal change in fluorescence spectrum and luminescence spectrum of Si-DMA of Example 1 incubated with TMPyP$_4$. The concentration of Si-DMA was 50 μM, and the concentration of TMPyP$_4$ was 5 μM. The light irradiation was performed using a 510- to 550-nm wavelength ray at an intensity of 0.07 W/cm$^2$ under magnetic stirring so as to generate singlet oxygen.

Figure 2:
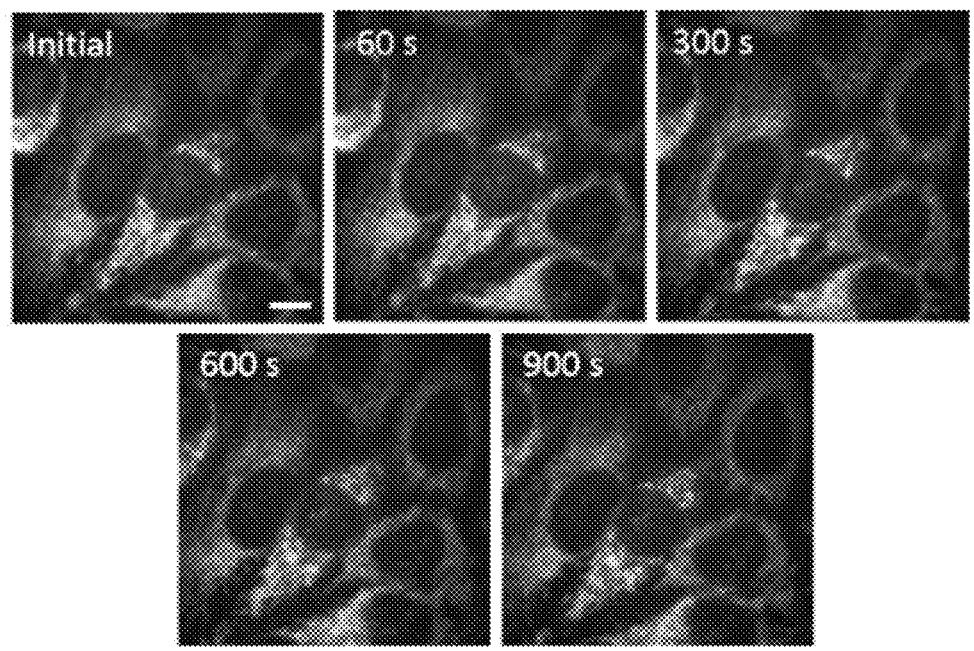
FIG. 2: Images showing the stability of Si-DMA in a Hela cell during 0.6 W/cm² light irradiation at a wavelength of 640 nm. The bar in the figure denotes 10 µm.

In FIGS. 1a) and 1c), the black arrows denote changes in absorption by peroxidation (solid line) of the anthracene structure and disaggregation of hydrogen aggregate (broken line). Further, in FIG. 1b), the red arrow shows an increase in fluorescence during 50-minute light irradiation. Conversely, FIG. 1d) shows that the fluorescence of Si-DMA did not increase even by light irradiation in the absence of TMPyP$_4$, and that the fluorescence of Si-DMA increased during 50-minute light irradiation in the presence of TMPyP$_4$ both in the methanol solution and the PBS solution. More specifically, color fading was not observed after 900 seconds had passed, thereby demonstrating stability. A similar stability was obtained when Si-DMA was introduced into HeLa cells, followed by light irradiation at a wavelength of 640 nm and an intensity of 0.6 W/cm2 (Si-DMA concentration=100 nM). FIG. 2 shows the results.

Figure 3:
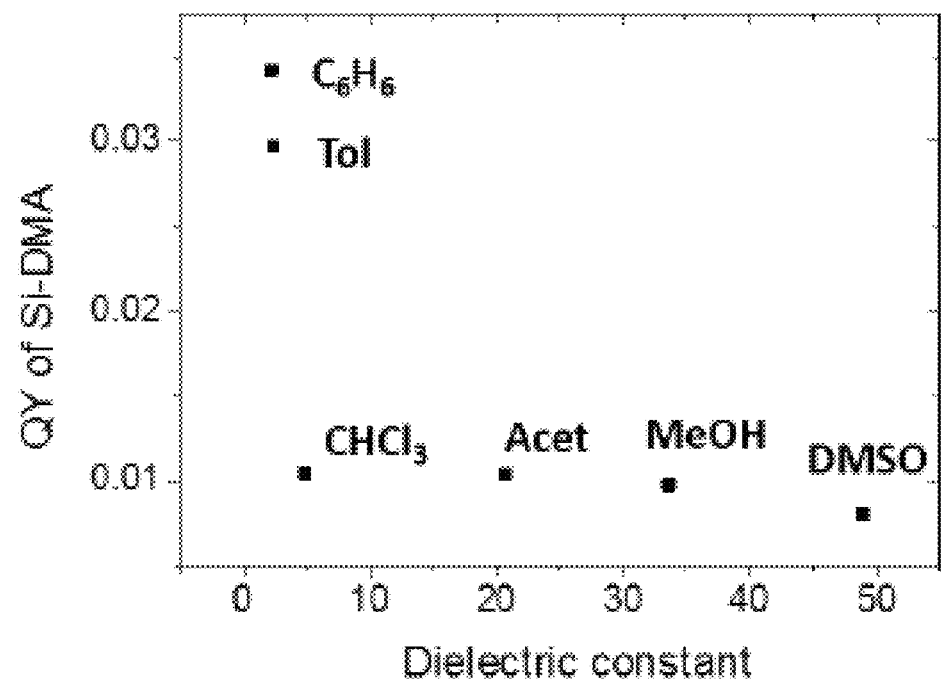
FIG. 3: A graph showing the fluorescence intensity of Si-DMA in various solvents in the absence of singlet oxygen.

As is clear from the above, fluorescence was hardly observed in the absence of singlet oxygen, ($\Phi_{fl}$=0.01; in methanol), and the excitation of silicon-rhodamine was cancelled due to photoinduced electron transfer caused by the anthracene structure. The fluorescence in the absence of singlet oxygen also depended on the type of solvent. The fluorescence intensity decreases when a polar solvent is used, thereby inhibiting erroneous signals. FIG. 3 shows the results ($\Phi_{fl}$: benzene: 0.034, toluene: 0.030, chloroform: 0.010, acetone: 0.010, methanol: 0.010, DMSO: 0.008).

Subsequently, Si-DMA was reacted with singlet oxygen, thereby forming Si-DMEP; as a result, photoinduced electron transfer was inhibited, thereby increasing the fluorescence intensity ($\Phi_{fl}$=0.17). In methanol, the fluorescence intensity increased about 18 times (in methanol), and about 22 times (in PBS) (FIGS. 1b) and 1d); red), and a loss of the anthracene structure was observed (FIG. 1a); black arrow).

Figure 4:
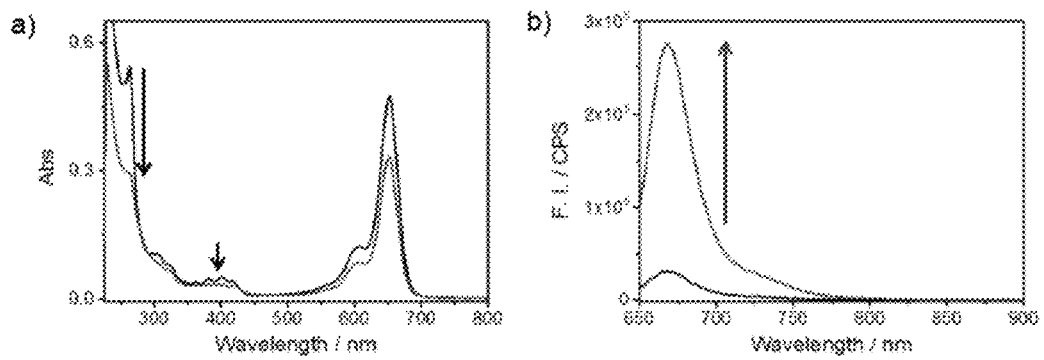
FIG. 4: Graphs showing the changes in absorption spectrum and fluorescence spectrum after introducing singlet oxygen by a chemical catalyst. a) shows the absorption spectrum, and b) shows the fluorescence spectrum.

Further, singlet oxygen was introduced into Si-DMA using a chemical catalyst. More specifically, singlet oxygen was introduced using 10 mM NaOCl and 10 mM H$_2$O$_2$. In this case as well, a spectral change similar to that in FIG. 1 was observed. FIG. 4 shows the results. The black arrow in FIG. 4a) and the red arrow in FIG. 4b) respectively show a loss of the anthracene structure, and an increase in the fluorescence of Si-DMA. The fluorescence increased about 10 times by 10-minute incubation using NaOCl and H$_2$O$_2$. By introducing a greater amount of singlet oxygen, more Si-DMA is expected to change into Si-DMEP.

As described above, the generation of singlet oxygen destroyed the anthracene structure, and fluorescence increased at a wavelength of about 650 to 700 nm. This revealed that the presence of singlet oxygen can be confirmed by the presence or absence of the luminescence of Si-DMA.

Experiment 2

Selectivity Test

A test was performed to confirm whether Si-DMA of Example 1 causes no self-oxidation of dye and is selectively responsive to singlet oxygen.

Figure 5:
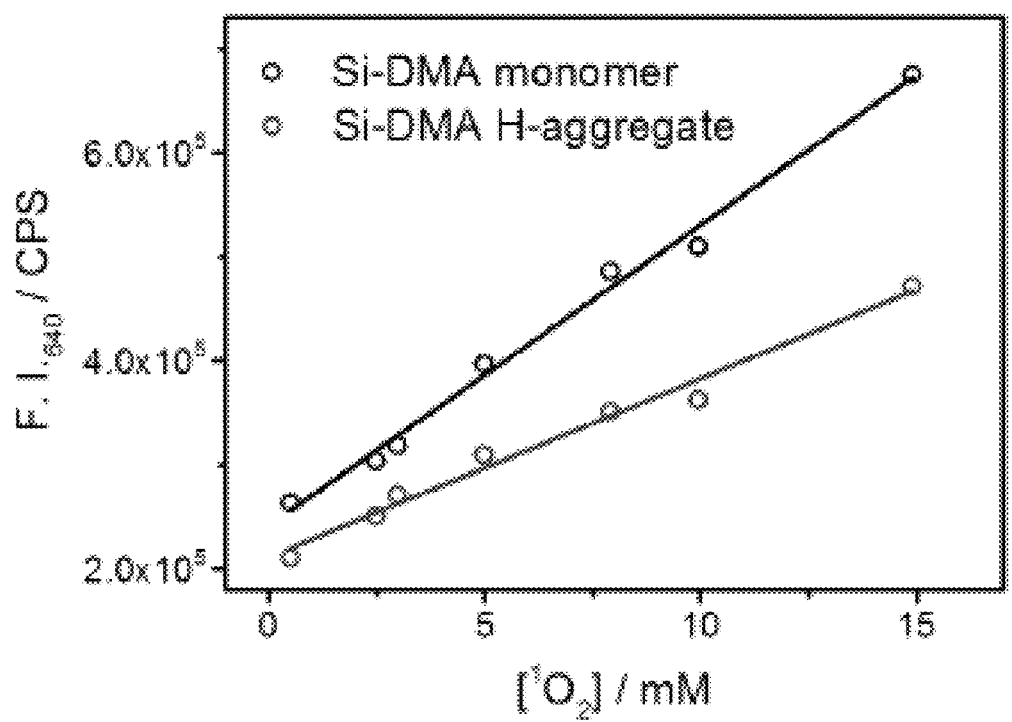
FIG. 5: A graph showing the fluorescence intensity of Si-DMA monomer and Si-DMA aggregate depending on the concentration of singlet oxygen generated by NaClO and $H_2O_2$.

First, an increase in fluorescence in proportion to the concentration of singlet oxygen generated by NaClO and $H_2O_2$ was observed both in an S-DMA monomer and an Si-DMA aggregate. FIG. 5 shows the results. In FIG. 5, the upper data shows the results of the S-DMA monomer, and the lower data shows the results of the Si-DMA aggregate. The measurement was performed by generating singlet oxygen using NaClO and $H_2O_2$ in a solution containing DMSO:methanol:tris buffer agent=1:49:50 (Si-DMA concentration=5 μM).

However, formation of aggregates decreases the effective concentration of the dye, thereby decreasing the reaction speed of Si-DMA. Therefore, a 5-μM Si-DMA solution was first prepared using a mixed solvent containing methanol and a pH 7.4 PBS buffer solution mixed at 1:1. In this solution, Si-DMA was present as a monomer. Subsequently, 10-mM solutions of various reactive oxygen species (ROS) ($^1O_2$, $O_2.^-$, $H_2O_2$, HOCl, ROO., and .OH) were prepared by adding the following additives to the 5-μM Si-DMA solution obtained above.

Figure 6:
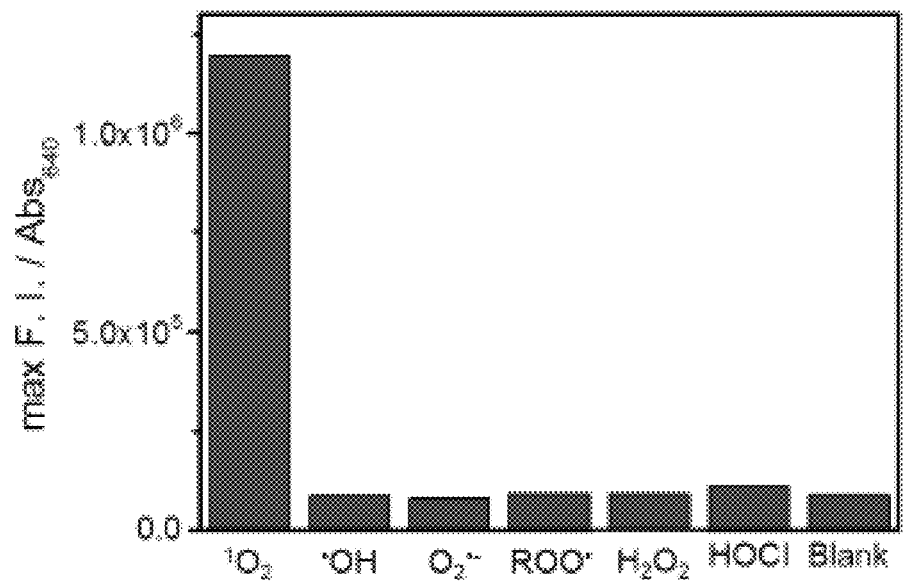
FIG. 6: A graph showing the fluorescence intensity of Si-DMA in the presence of various reactive oxygen species.

1. $^1O_2$: 10 mM NaOCl and 10 mM $H_2O_2$
2. $O_2.^-$: 10 mM $KO_2$
3. $H_2O_2$: 10 mM $H_2O_2$
4. HOCl: 10 mM NaOCl
5. ROO.: 10 mM 2,2-azobis(2-amidinopropane)dihydrochloride
6. .OH: 1 mM $FeSO_4.7H_2O$ and 10 M $H_2O_2$ Under intense magnetic stirring, each Si-DMA solution containing reactive oxygen species (ROS) was stored for 10 minutes in a dark room. Subsequently, the solutions were compared in terms of absorption upon light irradiation at a wavelength of 640 nm. FIG. 6 shows the resulting fluorescence intensity of Si-DMA in the presence of each reactive oxygen species.

The results revealed that the fluorescence intensity significantly increased in the presence of singlet oxygen, whereas the fluorescence intensities in the presence of other reactive oxygen species were merely similar to that in the absence of reactive oxygen (i.e., no increase in fluorescence was observed). This demonstrates that Si-DMA is useful as a fluorescent probe for selectively detecting only singlet oxygen among various reactive oxygen species.

Experiment 3

Time-Resolved Phosphorimetry

A sample of Rose Bengal and the Si-Me of Comparative Example 1 was prepared in a DMSO and methanol (1:9) solution placed in a 1×1×4 cm$^3$ quartz cell (the concentration of Rose Bengal=21.5 μM, and the concentration of Si-Me=250 μM).

Second harmonic oscillation (532 nm, 4 nsfwhm, 5.0 mJ·cm$^{-2}$ pulse$^{-1}$) generated by a Q-switched Nd YAG laser (Surelite II-10, Continuum) was used as an excitation light. The light-induced luminescence of the sample cell was condensed on a quartz lens via a monochromator, and subsequently introduced into a near-infrared photomultiplier tube module (H10330A-75; Hamamatsu Photonics K.K.).

Figure 7:
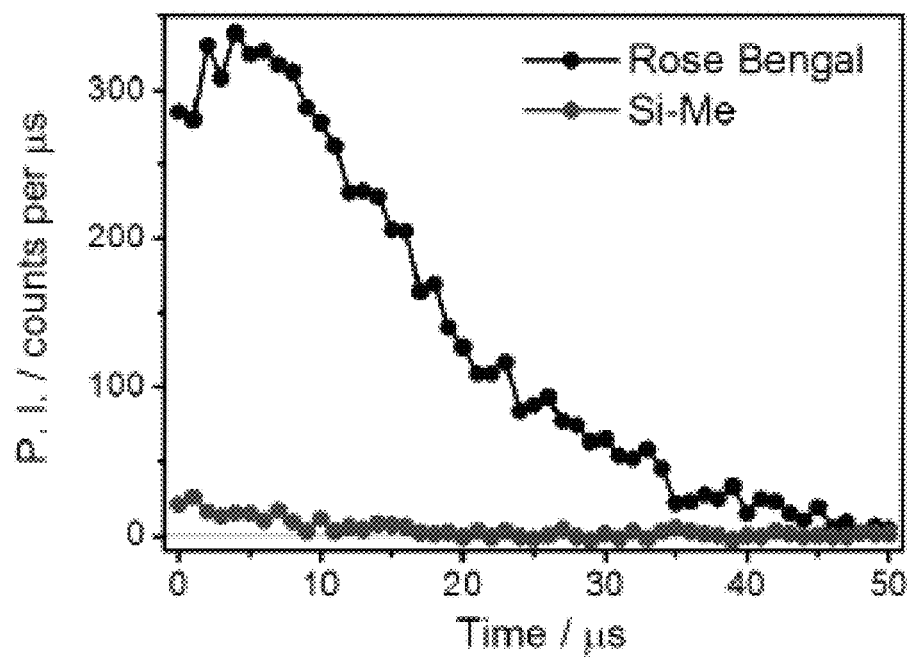
FIG. 7: A graph showing the results of time-resolved phosphorimetry with respect to Rose Bengal and Si-Me of Comparative Example 1.

After the amplification using a 350-MHz amplifier unit (SR445A; Stanford Research Systems), the output of the photomultiplier tube was sent to a gated photon counter (SR400; Stanford Research Systems) under direct PC control via a GPIB interface. In order to measure the lifetime of $^1O_2$, measurement was performed by changing the delay time between 0 to 50 μseconds at a gate width of 1.0 μsecond, and accumulating the results (repeated 5 times). FIG. 7 shows the results. In FIG. 7, the upper polygonal line shows the results of Rose Bengal, and the lower curve shows the results of Si-Me.

The results revealed that, in contrast to Rose Bengal ($\Phi_A$=0.76; in methanol), $\Phi_A$ of Si-Me was about 0.02, which was about one third of that of SOSG chromophore 2,7-dichlorofluorescein in which $\Phi_A$ is 0.06. This revealed that the fluorescent probe of the present invention having a silicon-rhodamine skeleton is capable of preventing erroneous signals due to the generation of luminescence by the fluorescent probe itself. $\Phi_A$ is a singlet oxygen generation quantum yield.

Experiment 4

Viable Cell Imaging

In order to monitor an increase in fluorescence upon light irradiation on Si-DMA of Example 1, irradiation on reactive oxygen species was performed while monitoring the probe using an IX81 inverted fluorescence microscope (Olympus Corporation) and 640-nm CW laser (Coherent). HeLa cells were introduced into a 35-mm μ-dish having a glass bottom (ibidi), and excited via an oil immersion objective (Olympus Corporation, PlanApo 100×/1.40 oil). The images of luminescence were collected and recorded by an EMCCD camera (Evolve 512; Roper Scientific) via a dichroic beam splitter (DI02-R635; Semrock) and a bandpass filter (HQ690/70; Chroma). During the data collection, the incubator (37° C., 5% $CO_2$) was kept in the same atmosphere using Chamlide TC (live cell counter). Pseudo fluorescence images were obtained by reprocessing moving-image files obtained from OriginPro 9.1 (OriginLab) and Image J.

In order to confirm the localization of the dye in a specific organelle, an objective scanning confocal microscope (PicoQuant, Micro Time 200) coupled with an Olympus IX71 inverted microscope was used. In a μ-slide 8-well (ibidi), HeLa cells were excited at two wavelengths, 405-/640-nm and 485-/640-nm, using a pulsed laser (PicoQuant) controlled by a PDL-800B driver (PicoQuant) via an oil immersion objective (Olympus Corporation, UPlanSAPo 100×/1.40 Oil/0.17/FN26.5). Subsequently, the luminescence was collected and detected by a single-photon avalanche photodiode (micro-optic device, PDM50CT and 100CT) equipped with a beam splitter (90% transmission, 10% reflection), an appropriate bandpass filter, and a 75-μm pinhole for spatial filtering to remove blurring signals. Two images of green and red channels were merged by OriginPro 9.1 (OriginLab) and Image J.

Figure 8:
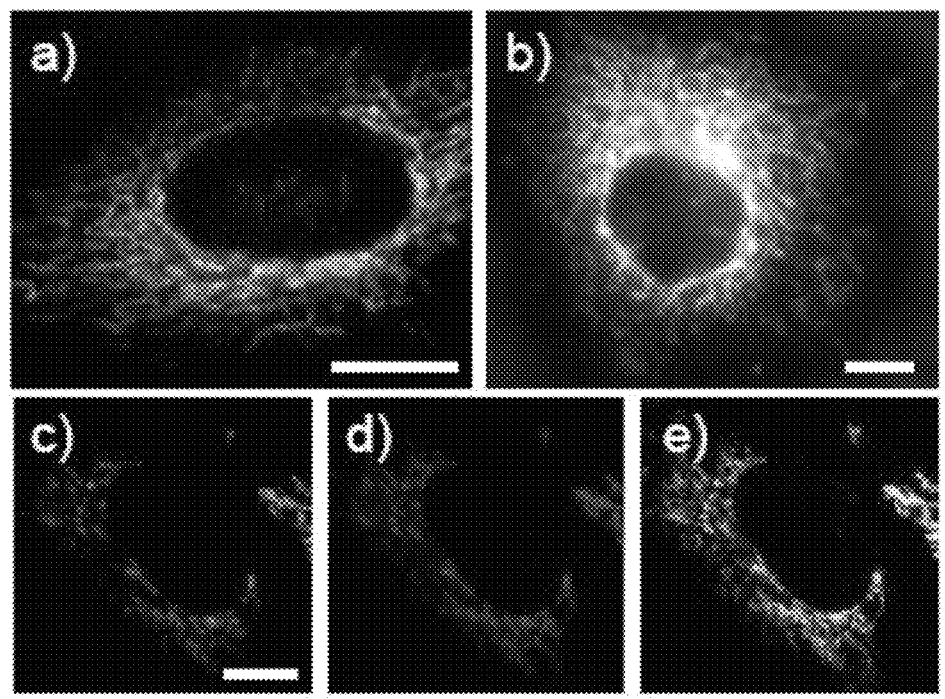
FIG. 8: Images showing the results of viable cell imaging in Experiment 4 using Si-DMA. a) shows the staining of a Hela cell at an Si-DMA concentration of 20 nM, and b) shows the staining of a Hela cell at an Si-DMA concentration of 100 nM. c) to e) show a Si-DMA localization test in mitochondria.
Figure 9:
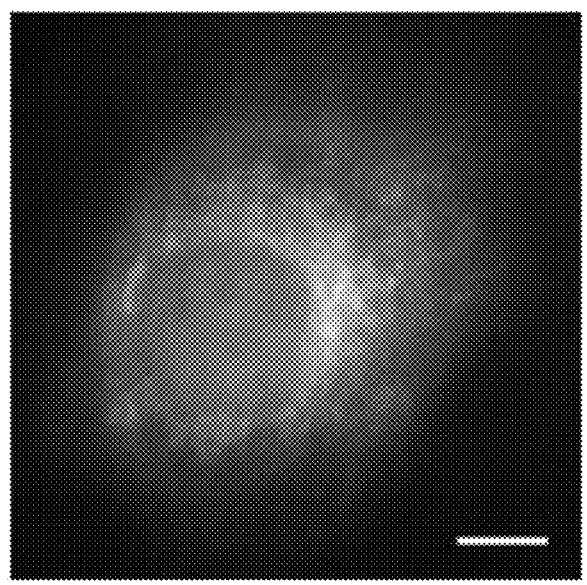
FIG. 9: An image showing the results of viable cell imaging in Experiment 4 using SOSG. The scale bar denotes 10 µm.

The results revealed that Si-DMA can be selectively localized in mitochondria. FIG. 8 shows the results. Conversely, although staining of HeLa cells was possible in a similar measurement using the trianion molecule SOSG, the staining was unclear even when a large amount (10 μM) of SOSG was used and therefore an accurate staining of the target object was not possible. FIG. 9 shows the results.

Experiment 5

Selectivity of Photosensitizer

Figure 10:
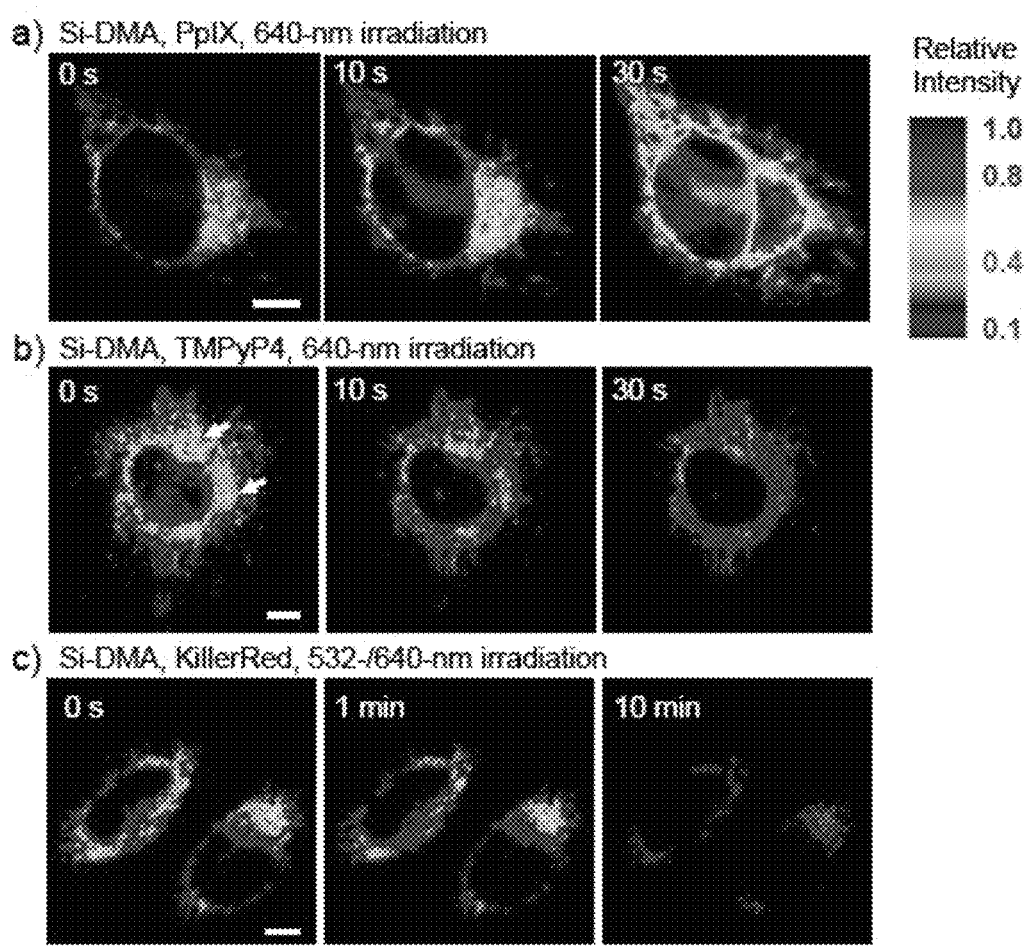
FIG. 10: Images showing the results of Experiment 5 (the difference in fluorescence due to the difference in photosensitizer).

On the night before the treatment, $0.2 \times 10^6$ HeLa cells were seeded on a 35-mm dish, and subjected to 4-hour incubation using a cell culture solution containing 150 μg/mL 5-aminolevulinic acid, 10% FBS, and 20 mM HEPES buffer, thereby preparing HeLa cells containing PpIX. The cells were further incubated for an hour in a cell culture solution containing 25 nM Si-DMA and 20 mM HEPES buffer. Light irradiation was performed for 30 seconds at 0.6 W/cm$^2$ using a 640-nm CW laser (Coherent) and a wide-view fluorescence microscope system mounted in an IX81 inverted microscope (Olympus Corporation). The signals obtained by Evolve 512 (EMCCD camera; Roper Scientific) were subjected to image-reprocessing using Image J, originPro program. FIG. 10a) shows the results.

Further, on the night before the treatment, $0.2 \times 10^6$ HeLa cells were seeded on a 35-mm dish, and subjected to 24-hour incubation as described above using a cell culture solution containing 10 μM TMPyP$_4$, 10% FBS, and 20 mM HEPES buffer, thereby preparing HeLa cells containing PpIX. The cells were further incubated for an hour in a cell culture solution containing 25 nM Si-DMA and 20 mM HEPES buffer. Light irradiation was performed for 30 seconds at 0.6 W/cm$^2$ using a 640-nm CW laser (Coherent) and a wide-view fluorescence microscope system mounted in an IX81 inverted microscope (Olympus Corporation). The signals obtained by Evolve 512 (EMCCD camera; Roper Scientific) were subjected to image-reprocessing using Image J, originPro program. FIG. 10b) shows the results.

Further, on the night before the treatment, $0.2 \times 10^6$ HeLa cells were seeded on a 35-mm dish, and pKillerRed-dMito vector (Evrogen) was introduced using Lipofectaimine®2000 (Invitrogen®), followed by 24-hour incubation as described above, thereby preparing HeLa cells containing PpIX. The cells were further incubated for an hour in a cell culture solution containing 25 nM Si-DMA and 20 mM HEPES buffer. Light irradiation was performed for 30 seconds simultaneously at 0.5 W/cm$^2$ and 0.6 W/cm$^2$ using a 640-/532-nm laser (Coherent) and a wide-view fluorescence microscope system mounted in an IX81 inverted microscope (Olympus Corporation). The signals obtained by Evolve 512 (EMCCD camera; Roper Scientific) were subjected to image-reprocessing using Image J, originPro program. FIG. 10c) shows the results.

Figure 11:
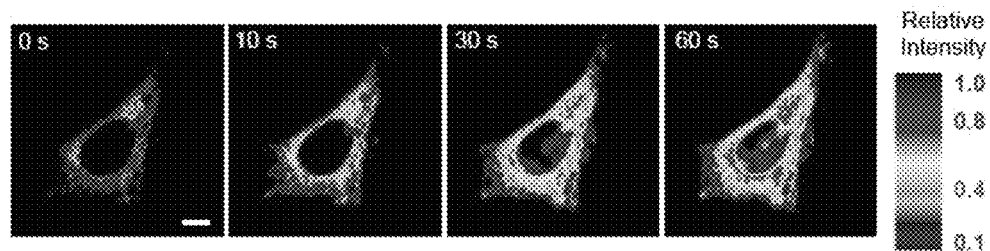
FIG. 11: Images showing the results of Experiment 5 (the Si-DMA concentration was changed to 100 nM, and PpIX was used as a photosensitizer).

This suggested that when PpIX localized in the mitochondrial inner membrane was used as a photosensitizer, the increase in the fluorescence of Si-DMA was rapidly (within 10 seconds) induced in the vicinity of the perinuclear region, and that, moreover, clear color rendering was accomplished. Similar results were observed when the Si-DMA concentration increased to 100 nM. FIG. 11 shows the results of this case.

Figure 12:
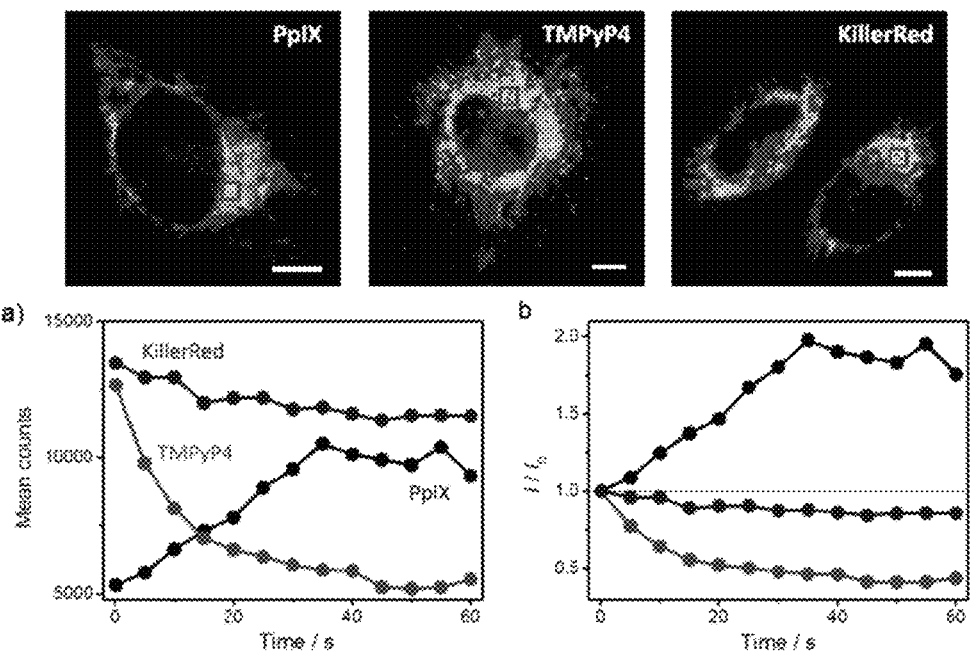
FIG. 12: Images showing the results of Experiment 5 (the number of pseudo colors for each type of photosensitizer, and the degree of increase or decrease of the number).

Further, in this Experiment Example, 60-second light irradiation was performed using three kinds of photosensitizers, and an average number of pseudo colors appeared in the photo and an increase thereof were measured. FIG. 12 shows the results. The results suggested that, during the light irradiation, the number of pseudo colors increased only in the sample using PpIX as a photosensitizer. It was thus suggested that this sample was capable of detecting singlet oxygen generated by light irradiation. When TMPyP$_4$ was used as a photosensitizer, the average number of pseudo colors decreased, thus showing an evident failure in the detection of singlet oxygen. Further, when KillerRed was used as a photosensitizer, fluorescence was observed even before the light irradiation, and the average number of pseudo colors gradually decreased with the light irradiation. It was thus suggested that, in this case, no fluorescence by light irradiation was confirmed and the detection of singlet oxygen failed.

Figure 13:
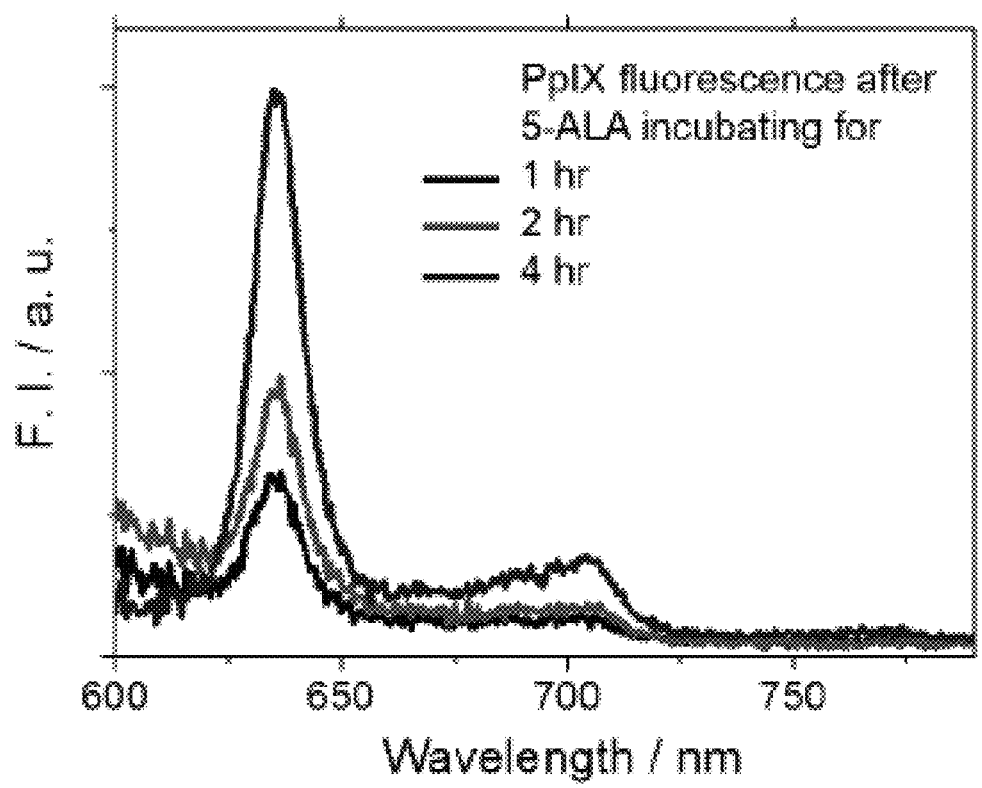
FIG. 13: A graph showing the results of Experiment 5 (changes in the fluorescence intensity depending on the incubation time).

FIG. 13 shows changes in fluorescence intensity depending on the incubation time when 5-aminolevulinic acid was used. As mentioned above, it was revealed that, as the incubation time increased, the fluorescence intensity of porphyrin (PpIX) biosynthesized in the cells by 5-ALA incubation increased, and that the fluorescence intensity was maximally increased by four-hour incubation.

We claim:

1. A fluorescent probe for detecting singlet oxygen, comprising a compound represented by Formula (1):

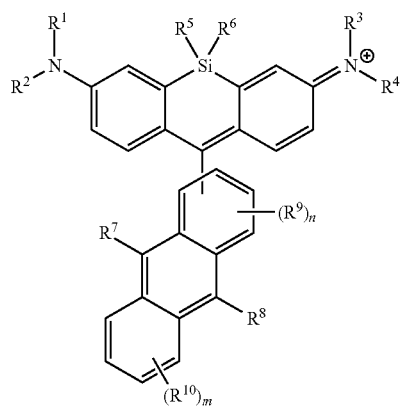

wherein $R^1$ to $R^4$ are the same or different, and each represents hydrogen, substituted or unsubstituted alkyl, substituted or unsubstituted alkenyl, substituted or unsubstituted alkynyl, or substituted or unsubstituted aryl; $R^5$ and $R^6$ are the same or different, and each represents hydrogen, hydroxy, halogen, substituted or unsubstituted alkyl, substituted or unsubstituted alkenyl, substituted or unsubstituted alkynyl, or substituted or unsubstituted aryl; $R^7$ and $R^8$ are the same or different, and each represents hydrogen, halogen, substituted or unsubstituted alkyl, substituted or unsubstituted alkenyl, substituted or unsubstituted alkynyl, substituted or unsubstituted aryl, substituted or unsubstituted alkoxy, or acid addition salt; $R^9$ and $R^{10}$ are the same or different, and each represents hydroxy, halogen, substituted or unsubstituted alkyl, substituted or unsubstituted alkenyl, substituted or unsubstituted alkynyl, substituted or unsubstituted aryl, or acid addition salt; n is an integer of 0 to 3; and m is an integer of 0 to 4.

2. The fluorescent probe according to claim 1, wherein the compound is represented by Formula (1A):

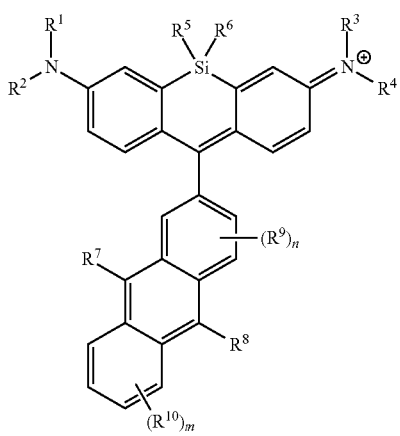

wherein $R^1$ to $R^{10}$, n, and m are as defined in claim 1.

3. The fluorescent probe according to claim 1 wherein each of $R^1$ to $R^8$ is a methyl, and n and m are both 0.

4. A singlet oxygen detection agent, comprising the fluorescent probe according to claim 1.

5. The singlet oxygen detection agent according to claim 4, wherein the singlet oxygen detection agent contains 10 to 500 nmol/L of the fluorescent probe.

6. A method for detecting singlet oxygen generated in a cell, comprising the steps of:
 (1) culturing a cell under a condition in which singlet oxygen is generated;
 (2) preparing and culturing a mixed culture solution containing the culture solution obtained in step (1) and the fluorescent probe of claim 1, wherein the concentration of the fluorescent probe is 10 to 500 nmol/L; and
 (3) irradiating the mixed culture solution obtained in step (2) with light.

7. The method for detecting singlet oxygen according to claim 6, wherein the condition in which singlet oxygen is generated in step (1) is a condition having a photosensitizes.

8. The method for detecting singlet oxygen according to claim 7, wherein the photosensitizer is protoporphyrin IX.

9. The method for detecting singlet oxygen according to claim 6, wherein the cell is a cancer cell.

10. The method for detecting singlet oxygen according to claim 6, wherein the method site-selectively detects singlet oxygen generated near a mitochondrial inner membrane in the cell.

11. A compound represented by Formula (1):

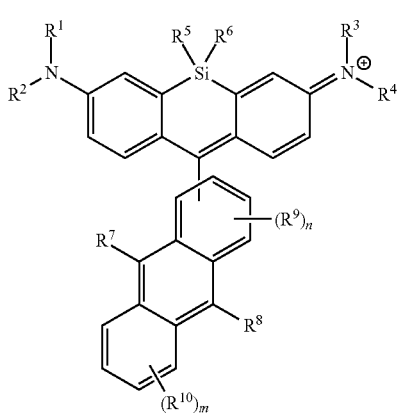

wherein $R^1$ to $R^4$ are the same or different, and each represents hydrogen, substituted or unsubstituted alkyl, substituted or unsubstituted alkenyl, substituted or unsubstituted alkynyl, or substituted or unsubstituted aryl; $R^5$ and $R^6$ are the same or different, and each represents hydrogen, hydroxy, halogen, substituted or unsubstituted alkyl, substituted or unsubstituted alkenyl, substituted or unsubstituted alkynyl, or substituted or unsubstituted aryl; $R^7$ and $R^8$ are the same or different, and each represents hydrogen, halogen, substituted or unsubstituted alkyl, substituted or unsubstituted alkenyl, substituted or unsubstituted alkynyl, substituted or unsubstituted aryl, substituted or unsubstituted alkoxy, or acid addition salt; $R^9$ and $R^{10}$ are the same or different, and each represents, hydroxy, halogen, substituted or unsubstituted alkyl, substituted or unsubstituted alkenyl, substituted or unsubstituted alkynyl, substituted or unsubstituted aryl, or acid addition salt; n is an integer of 0 to 3; and m is an integer of 0 to 4.

12. The compound according to claim 11, wherein the compound is represented by Formula (1A):

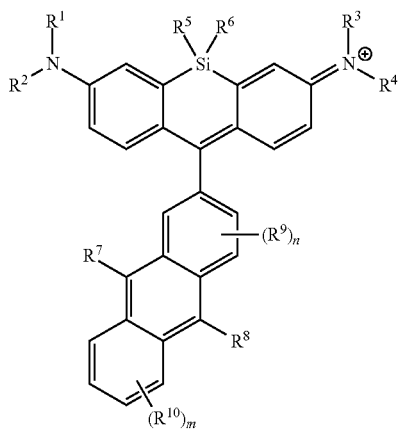

wherein $R^1$ to $R^{10}$, n, and m are as defined in claim 11.

13. A cell assay reagent, comprising the fluorescent probe of claim 1.

14. The singlet oxygen detection agent according to claim 4, which is a singlet oxygen detection agent generated near a mitochondrial inner membrane.

15. The singlet oxygen detection agent according to claim 4, which is color rendering agent of mitochondria.

16. The compound according to claim 11, wherein each of $R^1$ to $R^8$ is a methyl, and n and m are both 0.

17. A cell assay reagent, comprising the singlet oxygen detection agent of claim 4.

18. A cell assay reagent, comprising the compound of claim 11.

* * * * *